United States Patent [19]
Kawakami et al.

[11] Patent Number: 5,488,353
[45] Date of Patent: Jan. 30, 1996

[54] APPARATUS AND METHOD FOR IMPROVING THE AWARENESS OF VEHICLE DRIVERS

[75] Inventors: Yoshinaka Kawakami, Kariya; Yoshiharu Takigawa, Okazaki; Arihiro Isomura, Kariya; Kouichi Kamiya, Anjo; Katsunori Hamatani, Okazaki, all of Japan

[73] Assignee: Mitsubishi Jidosha Kogyo Kabushiki Kaisha, Tokyo, Japan

[21] Appl. No.: 177,863

[22] Filed: Jan. 4, 1994

[30] Foreign Application Priority Data

Jan. 6, 1993 [JP] Japan .................. 5-000785

[51] Int. Cl.⁶ .................................................. G08B 23/00
[52] U.S. Cl. .................................... 340/576; 340/575
[58] Field of Search ................................ 340/575, 576, 340/439; 128/691, 706, 639; 180/271, 272

[56] References Cited

U.S. PATENT DOCUMENTS

| | | | |
|---|---|---|---|
| 4,348,663 | 9/1982 | Yanagishima et al. | 340/576 |
| 4,359,725 | 11/1982 | Balogh et al. | 340/576 |
| 4,572,207 | 2/1986 | Yoshimi et al. | |
| 4,604,611 | 8/1986 | Seko et al. | 340/576 |
| 4,706,072 | 11/1987 | Ikeyama | 340/576 |
| 4,928,090 | 5/1990 | Yoshimi et al. | 340/575 |
| 5,311,877 | 5/1994 | Kishi | 340/576 |

FOREIGN PATENT DOCUMENTS

| | | |
|---|---|---|
| 2485364 | 12/1981 | France . |
| 2555042 | 6/1977 | Germany . |
| 61-2340 | 7/1979 | Germany . |
| 3826943 | 2/1990 | Germany . |
| 59-22537 | 2/1959 | Japan . |
| 56-2227 | 1/1981 | Japan . |
| 2159111 | 11/1985 | United Kingdom . |

*Primary Examiner*—Brent A. Swarthout
*Assistant Examiner*—Benjamin C. Lee

[57] ABSTRACT

An apparatus and method for a driver of a vehicle in which a level of awareness of the driver is determined, and compared with a reference value to determine a decrease in awareness. A warning is generated when driver awareness is low. The driver responds by terminating the warning. The reference value of the awareness determination means is corrected according to a response time of the driver to the warning.

12 Claims, 23 Drawing Sheets

APPARATUS AND METHOD FOR IMPROVING THE AWARENESS OF VEHICLE DRIVERS

BACKGROUND OF THE INVENTION

This invention relates to an apparatus and method for improving the awareness of vehicle drivers or other persons such as ship captains and airplane pilots.

Recently, as a result of road network improvements the moving ability of vehicles has been considerably improved and more people spend a considerable amount of time driving. In general, drivers tend to drive their vehicle regardless of whether they are tired. If the driver operates the vehicle for an extended time without rest, fatigue sets in, which leads to decreased awareness of the driver and therefore the possibility of an accident.

To prevent this, an apparatus has been proposed wherein a signal for requesting a driver's response is provided at a time interval, and a decrease in driver awareness is determined from a response time of the driver to the given signal. However, in such an apparatus, a response may be required while the driver is traveling on a city road or curved road where the driver must concentrate on driving, and therefore, the driver's response may be long even though the driver's awareness level is high.

Other conventional apparatus monitor the driver's physical condition and, when a normal operation limit is exceeded, the driver is notified. Such an apparatus is disclosed in Japanese Patent Publication Laid-open (Japanese OPI) 59-22537. A heartbeat rate is increased or decreased according to driving force, mental stress, or a sensation of fear. Therefore, in the apparatus disclosed in Japanese OPI 59-22537, the driver's heartbeat rate is measured by a heartbeat sensor, and a determination is made as to whether or not a period of pulsation is within a preset tolerable range to determine the level of awareness of the driver.

Japanese Patent Publication Laid-open (Japanese OPI) 56-2227 generates a preliminary warning when a monotonous driving condition is detected, and a true warning is generated when the driver's reaction time exceeds a predetermined time, thereby determining the driver's level of awareness in two steps.

In Japanese OPI 59-22537, the heartbeat rate of the driver during driving is compared with a preset reference value to determine the level of awareness of the driver, and the reference value is fixed. However, the heartbeat rate depends on the individual driver and is affected by road in operating conditions. When the reference value of the heartbeat rate for determining the level of awareness is fixed, and a warning is generated according to the determination result, a warning may be given when the level of awareness of the driver is high or the warning may not be given when the level of awareness is low.

Japanese OPI 56-2227 determines the level of awareness of the driver in two steps, wherein the level of awareness is determined independently, and the fact that a decrease in the driver's level of awareness may occur over time is not considered.

Therefore, there is a danger that when driving is continued after an indication of decreased awareness, for example, the output of a preliminary warning, the level of awareness cannot be determined, and an appropriate warning cannot be output according to the actual level of awareness of the driver.

A primary object of the present invention is to provide an apparatus and method for improving the awareness of vehicle drivers which solve the above-identified problems.

SUMMARY OF THE INVENTION

In accordance with the present invention which attains the above object, there is provided an apparatus for improving an awareness of vehicle drivers comprising: awareness determination means for determining a level of awareness of a vehicle driver and comparing the level of awareness with a reference value to determine a decrease in awareness, at least one warning means for generating a warning to the vehicle driver when the decrease in awareness is detected, warning termination means for terminating the warning, and reference value correction means for correcting the reference value of the awareness determination means according to a response time to the warning from the vehicle driver.

Therefore, the awareness determination means detects the awareness of the driver to determine an level and compares it with a reference value to determine a decrease in awareness, the warning control means controls warning means according to an output of the awareness determination means and, if the level of awareness of the driver decreases, gives a warning to increase the driver awareness. The driver can terminate the generation of the warning and reference value correction means corrects the reference value according to the response time to the warning by the driver.

Further, the apparatus according to the present invention comprises heartbeat rate detection means for detecting a heartbeat rate of the driver of the vehicle, heartbeat awareness determination means for comparing the heartbeat rate determined by the heartbeat rate detection means with a reference value to determine a decrease in awareness of the driver, warning means for warning the driver, warning control means for controlling the warning means according to the comparison by the heartbeat awareness determination means, warning termination means for terminating the warning by the warning means, and reference value correction means for correcting the reference value of the heartbeat awareness determination means according to a response time to the warning from the driver.

Therefore, the heartbeat awareness determination means detects the heartbeat rate of the driver of the vehicle to determine an index and compares the index with a reference value to determine a decrease in awareness of the driver, and the warning control means controls the warning means according to the comparison by the heartbeat awareness determination means and outputs a warning to improve the awareness if the level of awareness of the driver is low. At this moment, the driver can terminate the warning by warning termination means, and the reference value correction means corrects the reference value of the heartbeat awareness determination means according to a response time to the warning from the driver.

Further, the apparatus of the present invention comprises a steering angle sensor for detecting a steering angle of the vehicle, steering angle data processing means for calculating a frequency distribution of the steering angle and extracting a predetermined frequency area to determine a steering characteristic parameter of the driver, steering awareness determination means for comparing the steering characteristic parameter with a reference value to determine a decrease in awareness of the driver, warning means for warning the driver, warning control means for controlling the warning means according to the comparison by the steering awareness determination means, warning terminating means for terminating the warning by the warning means, and reference value correction means for correcting the reference value of the steering awareness determination means according to a response time to the warning from the driver.

Therefore, the steering awareness determination means determines the steering characteristic parameter of the driver from the steering angle signal and compares the steering characteristic parameter with a reference value to determine a decrease in awareness of the driver, and the warning control means controls the warning means according to the comparison by the steering awareness determination means and outputs a warning to improve the awareness if the driver's level awareness is low. At this moment, the driver can terminate the warning by the warning terminating means, and the reference value correction means corrects the reference value of the steering awareness determination means according to a response time to the warning from the driver.

Further, a method for determining an awareness of the present invention comprises the steps of: determining a level of awareness of a driver of a vehicle and comparing the level of awareness with a reference value to determine a decrease in awareness; outputting a warning to the driver; terminating the warning upon receipt of a response from the driver; and correcting the reference value according to a response time to the warning from the driver.

In the above-described invention, the reference value for determining the awareness can be set according to individual level of the driver,-operating conditions, and changes in awareness over time to determine the awareness, thereby improving the accuracy of awareness determination.

DETAILED DESCRIPTION OF THE PREFERRED EMBODIMENT

An embodiment of the present invention will now be described in detail with reference to the drawings.

Figure 1:
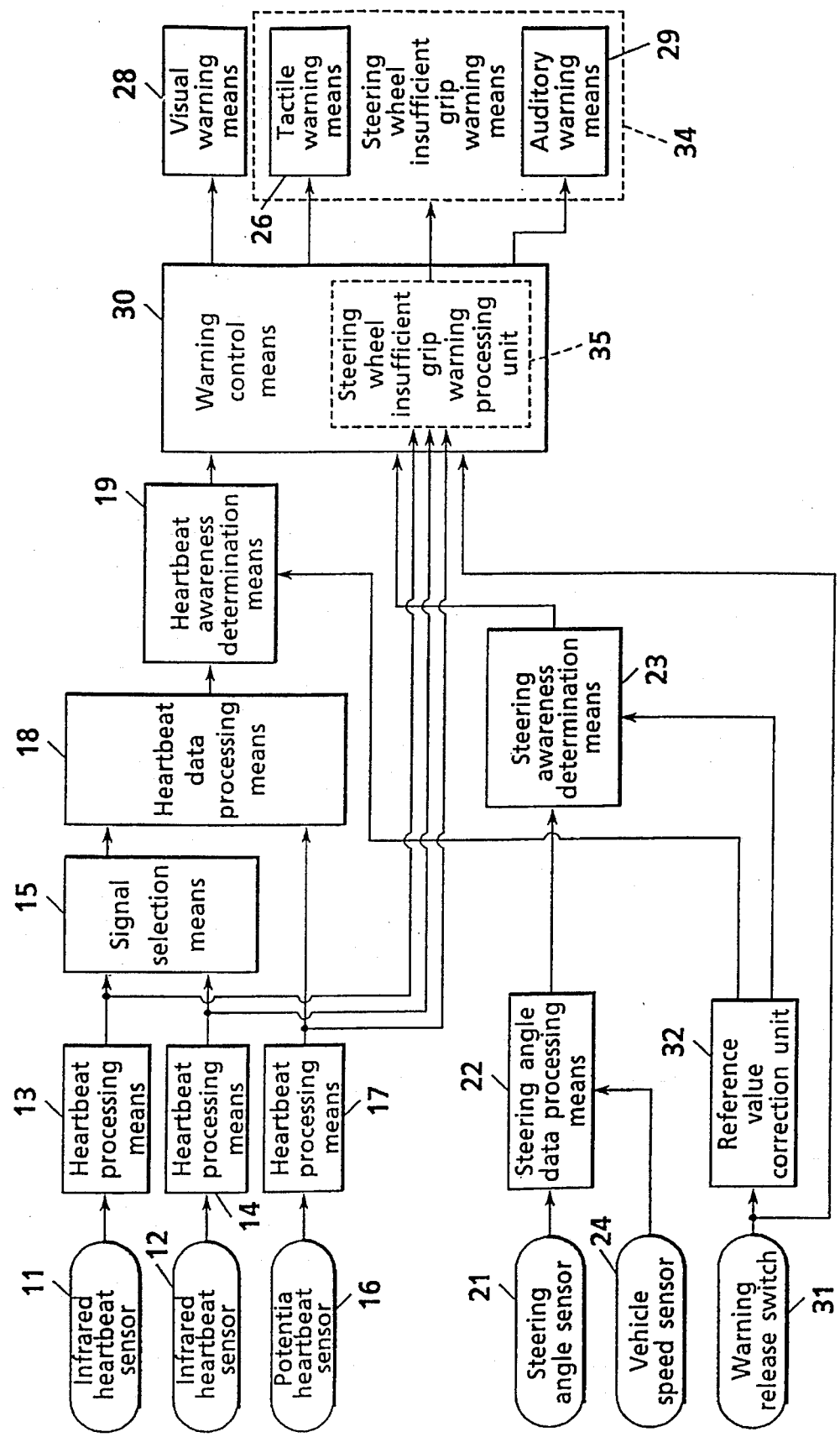
FIG. 1 is a block diagram showing the structure of an embodiment of the apparatus for improving the awareness of vehicle drivers according to the present invention.
Figure 2:
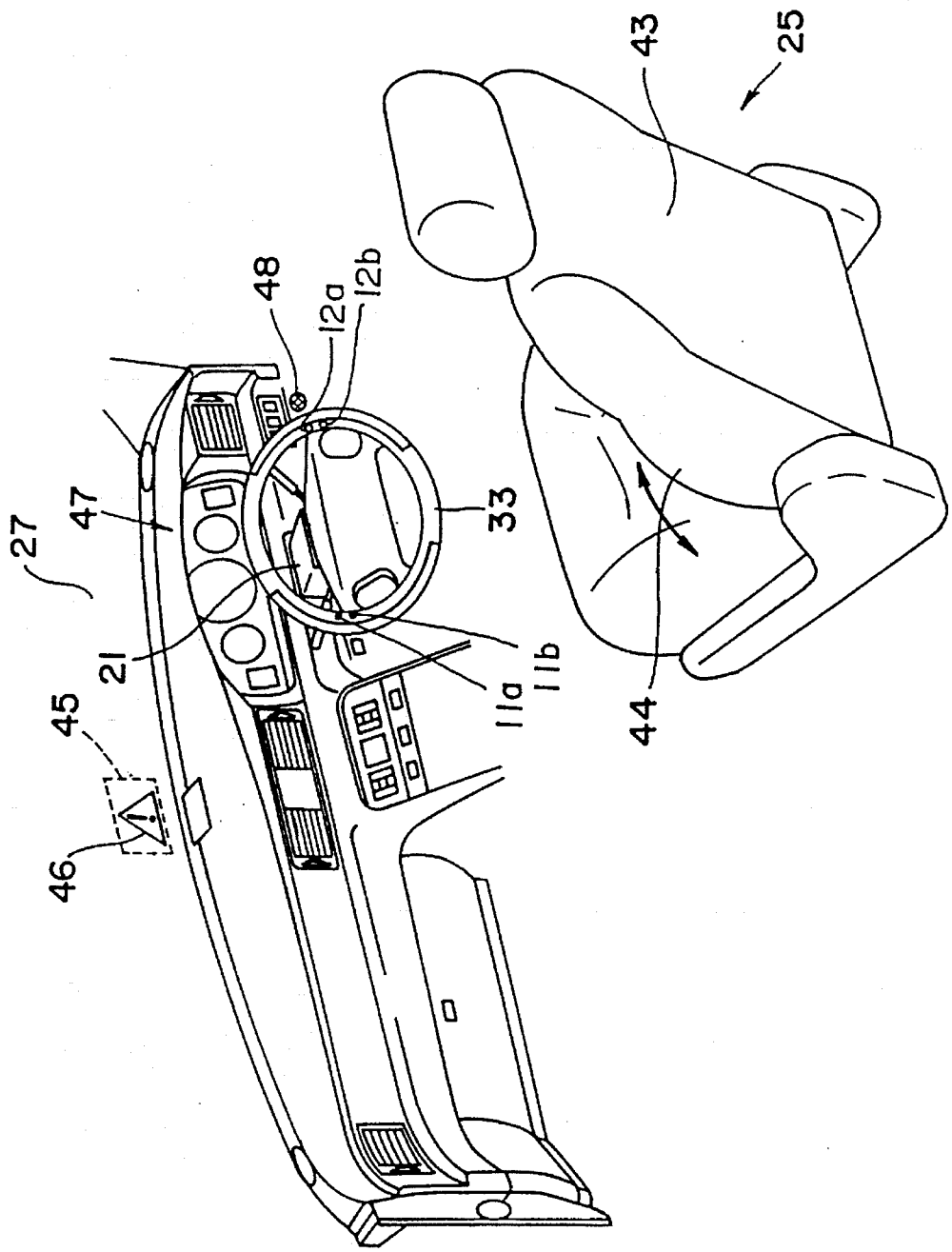
FIG. 2 is a schematic perspective view showing appearance of a vehicle interior in the embodiment.

FIG. 1 is a flow chart of an embodiment in which the awareness determination apparatus of the present invention is applied to an apparatus for improving the awareness of vehicle drivers, and FIG. 2 is a schematic view showing the interior of the vehicle room in this embodiment. A pair of right and left infrared heartbeat sensors 11 and 12 for detecting heartbeat pulses of the driver (not shown) are connected with heartbeat processing means 13 and 14 for receiving detection signals from the infrared heartbeat sensors 11 and 12 and calculating a heartbeat rate of the driver, and the heartbeat processing means 13 and 14 are connected to signal selection means 15, which selects one of the from output signals from either the heartbeat processing means 1S or 14. A potential heartbeat sensor 16, which is different from the heartbeat sensors 11 and 12, is connected to heartbeat processing means 17 which receives a detection signal from the potential heartbeat sensor 16 and calculates a heartbeat rate of the driver. The signal selection means 15 and the heartbeat processing means 17 are connected with heartbeat data processing means 18 for calculating an average value of the driver's heartbeat rate and a variance thereof according to output signals from the signal selection means 15 and the heartbeat processing means 17, and the heartbeat data processing means 18 is connected to heartbeat awareness determination means 19 for determining an awareness of the driver according to the calculations made by the heartbeat data processing means 18.

Further, a steering angle sensor 21 for detecting a deviation from a neutral position of a steering shaft 20 (hereinafter referred to as "steering angle") is connected to steering angle data processing means 22 which receives a detection signal from the steering angle sensor 21 and calculates a parameter of frequency analyzed steering component, and the steering angle data processing means is connected to steering awareness determination means for determining an awareness of the driver according to a calculated result from the steering angle data processing means 22.

Further, the steering angle data processing means 22 of the present embodiment is connected to a vehicle speed sensor 24 for detecting a traveling speed (hereinafter referred to as "vehicle speed") of the vehicle, and a detection signal from the vehicle speed sensor 24 is also input to the steering angle data processing means 22.

Further, the vehicle of the present embodiment is provided with tactile warning means 26 for generating a warning according to deformation of a driver's seat 25, and visual warning means 28 for displaying a warning on a front window 27 of the vehicle, and auditory warning means 29 for generating an audible. These three warning means 26, 28, and 29 are connected to the heartbeat awareness determination means 19 and the steering awareness determination means 29, wherein awareness signals are generated by the heartbeat awareness determination means 19 and the steering awareness determination means 29, and data reflecting the awareness of the driver, are output to warning control means 30, and the warning control means 30 controls operation of the three warning means 26, 28, and 29 according to the awareness signals generated by the heartbeat awareness determination means 19 and the steering awareness determination means 23.

In addition, a warning release switch 31 is provided in the vehicle interior for the driver to terminate warnings output by the three warning means 26, 28, and 29, and the warning release switch 31 is connected to the warning control means 30 and a reference value correction unit The reference value correction unit 32 is connected to the heartbeat awareness determination means 19 and the steering awareness determination means 29, and data calculated by the reference value correction unit 32 is input to the heartbeat awareness determination means 19 and the steering awareness determination means 23.

In the present embodiment, the above two types of heartbeat sensors 11, 12, and 16 are individually mounted at predetermined positions on a steering wheel 33. Therefore, a mechanism for prompting the driver to grip the steering wheel 33 correctly is provided, because the driver's heartbeat pulse cannot be detected, especially with the potential heartbeat sensor 16, unless the driver grips the steering wheel 33 with both hands at the predetermined positions.

Specifically, the vehicle of the present embodiment is provided with steering wheel grip defect warning means whose operation is controlled by the warning control means 30. The steering wheel grip defect warning means 34 of the present embodiment uses the two warning means 26 and 29. Further, warning control means 30 includes a steering wheel grip defect warning processing unit 95 which receives output signals from the heartbeat processing means 13, 14, and 17 determining whether or not the driver is griping the steering wheel 33 correctly according to output signals from the heartbeat processing means 13, 14, and 17. The warning control means 30 operates the steering wheel grip defect warning means 34 when it is determined that the driver is not gripping the steering wheel 33 correctly, and automatically stops operation of the steering wheel grip defect warning means 34 when it is determined that the driver is gripping the steering wheel 33 correctly.

Figure 3:
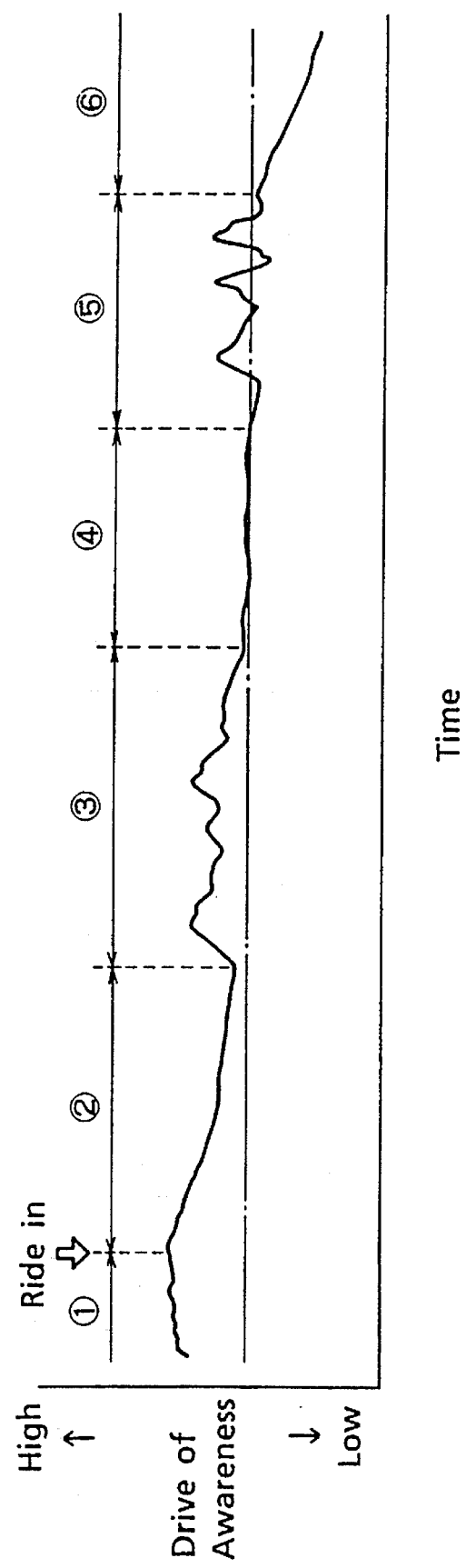
FIG. 3 is a graph showing changes in driver awareness over time.

In general, it is well known that driver awareness gradually decreases during a trip and the decrease is often accelerated due to traveling on a monotonous, deseated road for an extended time. An example of changes over time in driver awareness is illustrated in FIG. 3. The area (1) indicates a period before the trip, (2) indicates an awareness decreasing area as a result of continued driving, (3) indicates an area where awareness increases due to stress resulting from beginning the trip or stress from driving on a city road, (4) indicates an area where awareness is stable during traveling on a less crowded, monotonous road or a highway, (5) indicates an area where the awareness of the driver varies because the driver feels sleepy, and (6) indicates an area where the driver is completely unaware because the driver is asleep.

As can be seen from FIG. 3, normally there is an area (5) where the driver awareness increases and decreases because the driver feels sleepy before an area (6) where the driver actually falls asleep, and there is an area (4) where the awareness of the driver is stable before the driver begins to feel sleepy. That is, the awareness of the driver may be continuously monitored to estimate the area of stable awareness, and a transition area where the driver's awareness varies a great deal may be predicted from the area of stable awareness, and a warning can be output to prevent the driver from falling asleep.

Based on these findings, changes in awareness shown in FIG. 3 are estimated according to detection signals from the two types of heartbeat sensors 11, 12, and 16, and the two types of heartbeat sensors 11, 12, and 16 in the present embodiment are incorporated in predetermined positions of the steering wheel 33.

The infrared heartbeat sensors 11 and 12 which individually function independently utilize a reflection of infrared light by hemoglobin in pulsating blood in the vessel. In order to detect the amount of infrared light periodically varying according to the heartbeat, the sensors mainly comprise light projection units 11a and 12a for projecting infrared light and light reception units 11b and 12b for receiving the infrared light, individually incorporated on the right and left sides of the steering wheel 33. However, since the structure thereof and the like are already known in Japanese OPI 59-22597 and the like, a detailed description thereof is omitted.

The potential heartbeat sensor 16 detects a voltage pulse generated by a contraction of the myocardium between both hands of the driver as a pulsed voltage by a pair of electrodes 16a and 16b incorporated in the steering wheel 33 and, since the structure is known in Japanese OPI 59-25729 and the like, further description thereof is omitted.

Since the above-described infrared heartbeat sensors 11 and 12 may malfunction when strong sunlight is applied to the steering wheel 33, and the potential heartbeat sensor 16 cannot detect the driver's heartbeat if the driver does not grip the steering wheel 33 correctly by both hands, in the present embodiment these two types of heartbeat sensors 11, 12, and 16 are combined as will be described below to accurately detect the driver's heartbeat.

The heartbeat processing means 1S and 14 calculate the driver's heartbeat rate according to detection signals from the infrared heartbeat sensors 11 and 12, and similarly the heartbeat processing means 17 calculates the driver's heartbeat rate according to a detection signal from the potential heartbeat sensor 16. The calculations performed by the heartbeat processing means 13, 14, and 17 are basically the same, in which abnormal detection signals are appropriately corrected to calculate a heartbeat pulse interval (hereinafter referred to as "pulse interval") and the heartbeat rate corresponding to the pulse interval.

Figure 4:
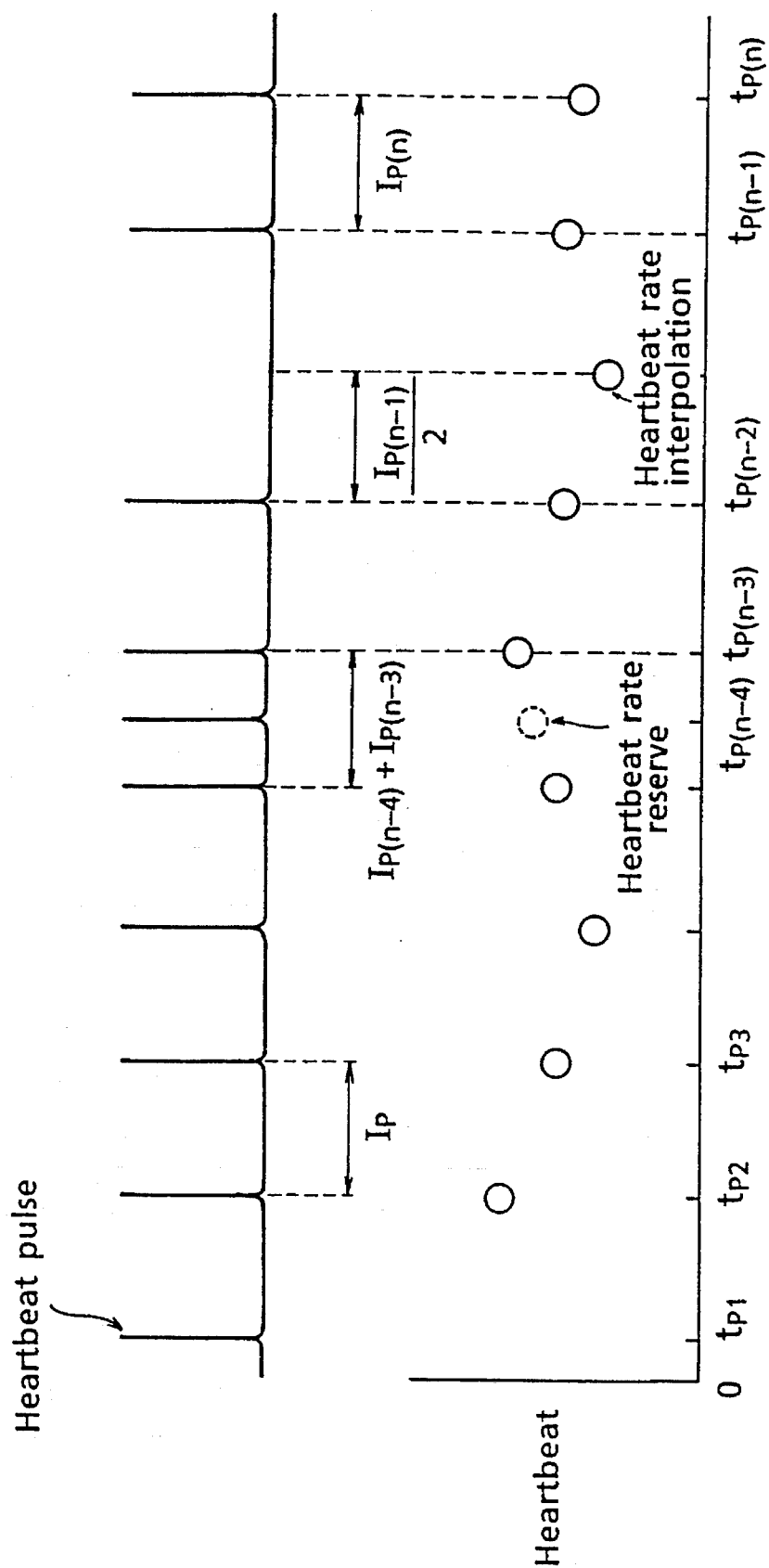
FIG. 4 is a schematic view showing a relationship between heartbeat pulse from a heartbeat sensor and heartbeat rate data calculated by heartbeat processing means.

FIG. 4 shows a relationship between heartbeat data calculated by the heartbeat processing means 13, 14, and 17 and the heartbeat pulses detected by the heartbeat sensors, for example, when the pulse interval suddenly becomes shorter than the previously measured pulse interval, the heartbeat calculation according to the pulse interval at that time is temporarily reserved, when the sum of the next measured pulse interval and the previous pulse interval is almost the same as the previous pulse interval, the previous heartbeat pulse information is determined to be due to noise, and the previous heartbeat data is canceled. For example, pulse intervals $I_{P(n-4)}$ and $I_{P(n-3)}$ at time $t_{P(n-4)}$ and a following time $tP_{(n-3)}$ are abnormally shorter than a past pulse interval $I_P$. As a result, the heartbeat rate calculated at the time $t_{P(n-4)}$ is reserved and, when the sum of the two pulse intervals $I_{P(n-4)}$ and $I_{P(n-3)}$ is almost the same as the past pulse interval, the heartbeat pulse at time $t_{(n-4)}$ is determined to be due to noise, and the heartbeat data at time $t_{P(n-4)}$ is canceled. Further, when the pulse interval suddenly becomes longer, when the next measured pulse interval is almost the same as the past pulse interval, half of the time of the previous pulse interval is added to the time at which the pulse interval before the previous pulse interval was calculated to interpolate heartbeat data at that time. For example, when the pulse interval at time $t_{P(n-1)}$ is abnormally longer than the past pulse interval $I_P$, when a pulse interval $I_{P(n)}$ at time $t_{P(n)}$ at which the next heartbeat pulse is detected is almost the same as the past pulse interval IP, it is determined that a normal heartbeat pulse could not be detected between the previous time and the time before previous time, and half of the time of the previous pulse interval $I_{P(n-1)}$ is added to time $t_{P(n-2)}$ at which the heartbeat pulse before the previous time was detected to calculate a heartbeat rate at this point of time.

Figure 5:
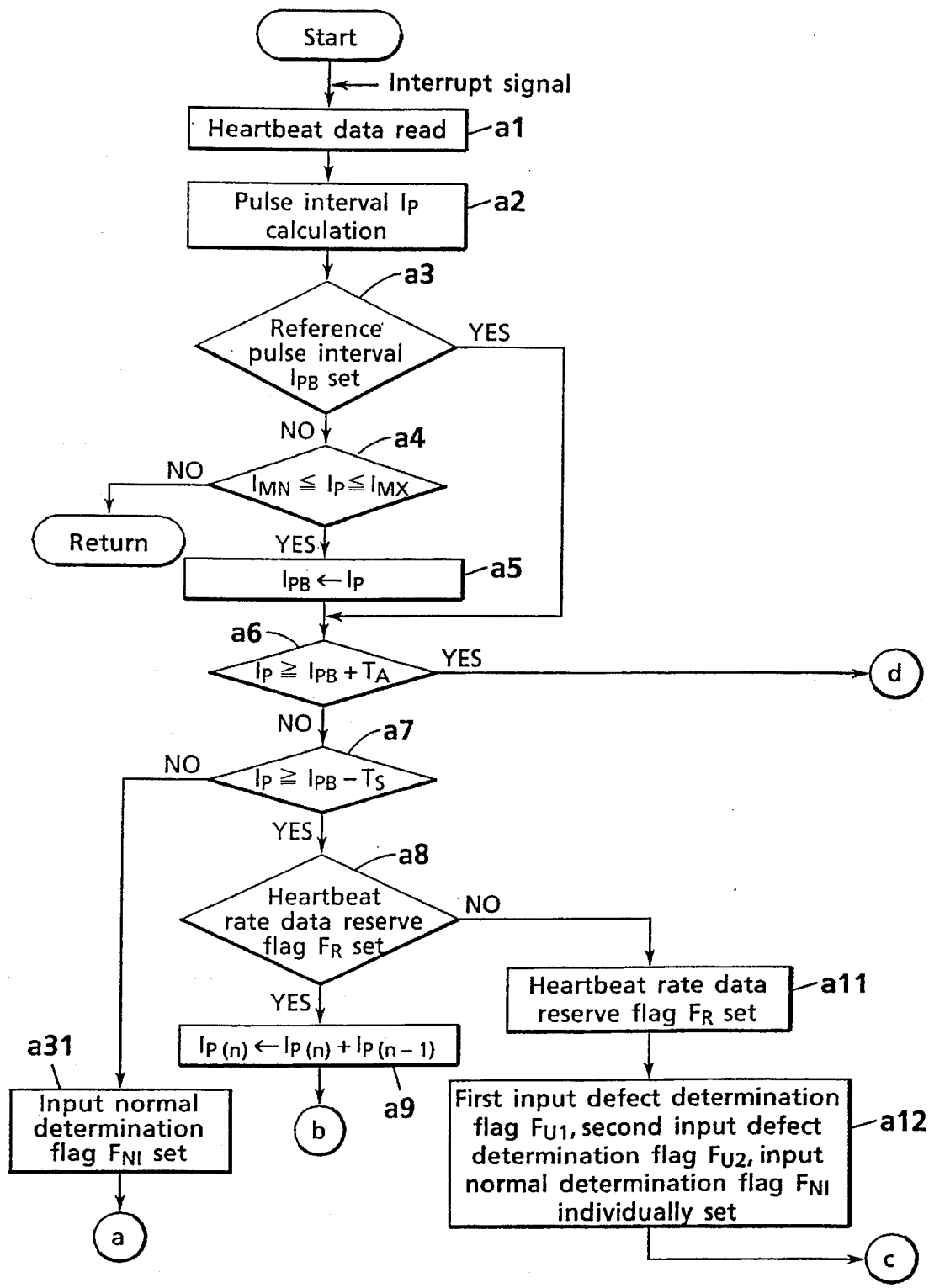
FIG. 5 is a flow chart showing processing performed by the heartbeat processing means of the embodiment along with FIGS. 6 and 7.
Figure 6:
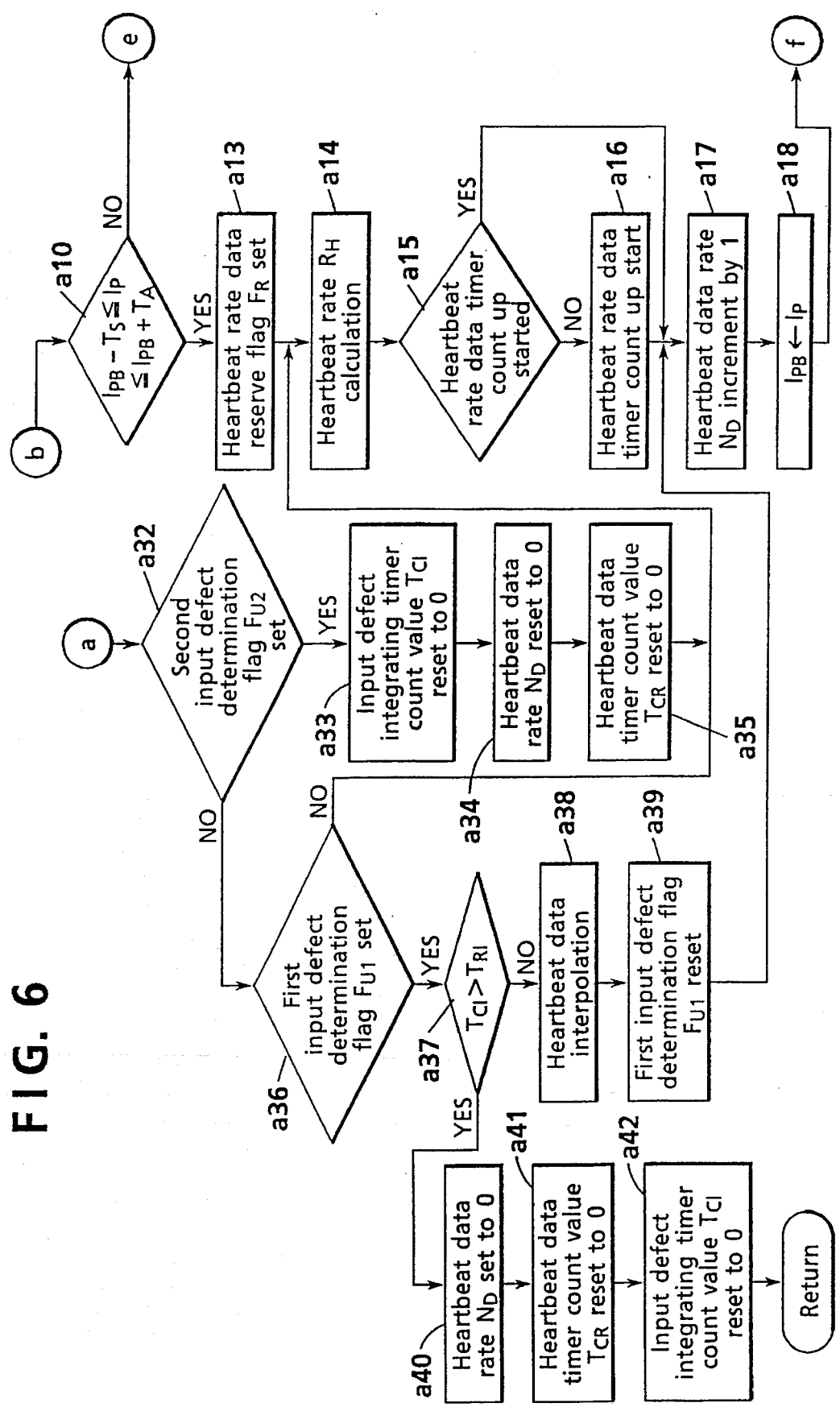
FIG. 6 is a flow chart showing processing performed by the heartbeat processing means of the embodiment along with FIGS. 5 and 7.
Figure 7:
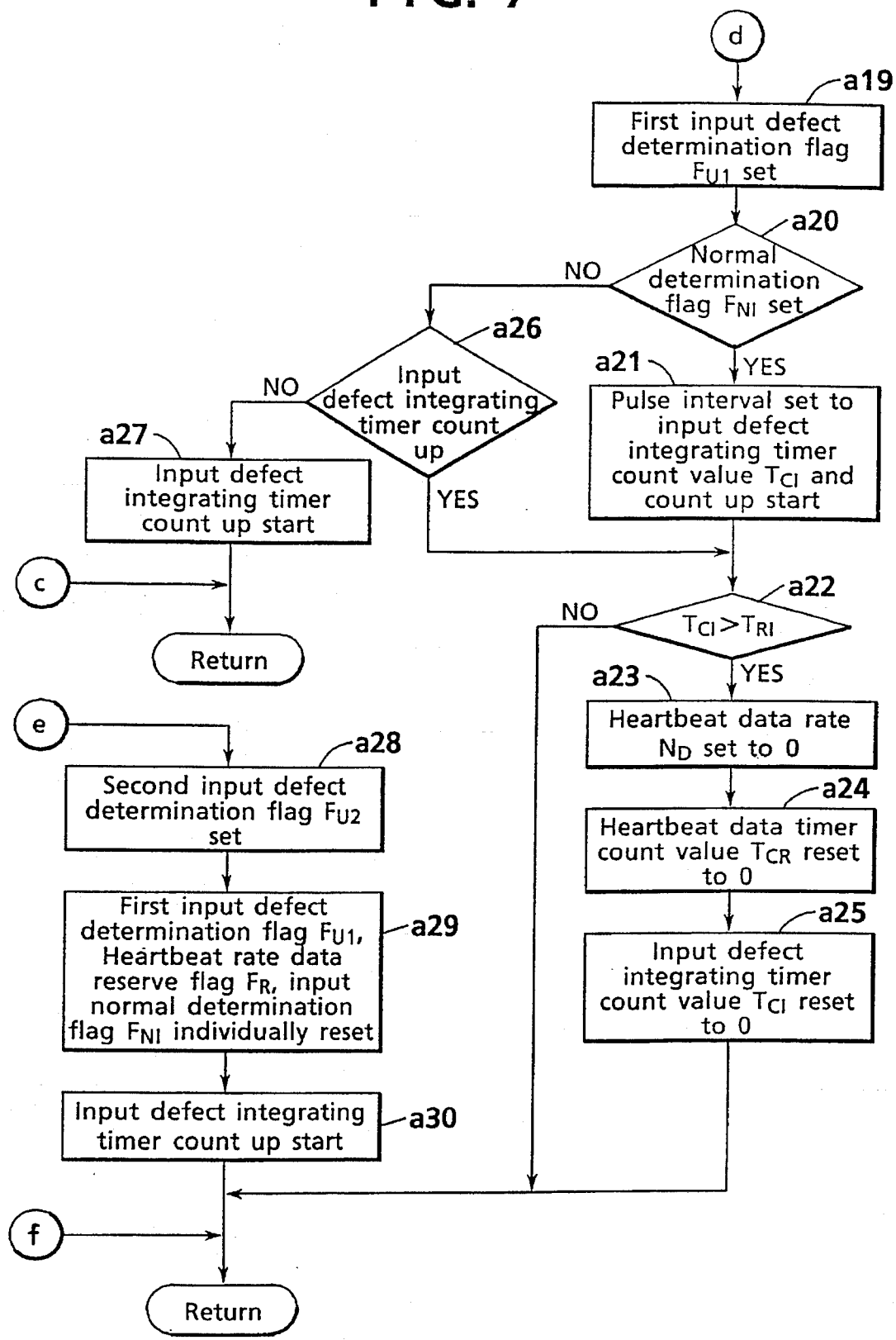
FIG. 7 is a flow chart showing processing performed by the heartbeat processing means of the embodiment along with FIGS. 5 and 6.

The processing flow of the heartbeat processing means 13, 14, and 17 is shown in FIGS. 5 to 7. Processing by the heartbeat processing means 13, 14, and 17 in the present embodiment is made in a predetermined period, for example, every time at an interrupt signal of every 15 msec. First, in step a1, the detection time $t_P$ of a heartbeat pulse detected by the heartbeat sensors 11, 12, and 16 is read, in step a2, the present pulse detection time $t_{P(n)}$ is subtracted by the previous pulse detection time $t_{P(n-1)}$, and the present pulse interval IP(n) according to the following equation:

$$I_{P(n)} = t_{P(n)} - t_{P(n-1)}.$$

Then, it is determined in step a3 whether or not a pulse interval reference value $I_{PB}$ is set, however, since the pulse interval reference value $I_{PB}$ is not set at the beginning, processing proceeds to step a4, where a determination is made as to whether or not the pulse interval $I_{P(n)}$ is between a preset minimum pulse interval $I_{MN}$, For example, 600 msec, and a maximum pulse interval $I_{MX}$, for example, 1200 msec.

When it is determined in step a4 that the pulse interval $I_{P(n)}$ is not between the minimum pulse interval and the maximum pulse interval $I_{MX}$, that is, the pulse interval $I_{P(n)}$ calculated in step a2 is abnormal, processing returns to step a1 after the above-described interrupt signal of a predetermined period. When it is determined in step a4 that the pulse interval $I_{P(n)}$ is between the minimum pulse interval IMN and the maximum pulse interval $I_{MX}$, that is, the pulse interval $I_{P(n)}$ calculated in step a2 is a normal value, the pulse interval $I_{P(n)}$ calculated in step a2 is adopted as the reference pulse interval $I_{PB}$ in step a5, and a determination is made in step a6 as to whether or not the present pulse interval $I_{P(n)}$ is longer than the sum of the reference pulse interval $I_{PS}$ and a preset additional time $T_A$, for example, 250 msec. Also, when it is determined in step a3 that the reference pulse interval $I_{PB}$ is set, processing proceeds to step a6.

When it is determined in step a6 that the present pulse interval $I_{P(n)}$ is shorter than the sum of the reference pulse interval $I_{PB}$ and the preset additional time $T_A$, that is, the value of the presently calculated pulse interval $I_{P(n)}$ is normal, a determination is made in step a7 as to whether or not the pulse interval $I_{P(n)}$ is shorter than a value of the reference pulse interval $I_{PB}$ subtracted by a preset subtraction time $T_s$, for example, 250 msec, and when it is determined in step a7 that the pulse interval $I_{P(n)}$ is less than the reference pulse interval $I_{PB}$ subtracted by the preset subtraction time $T_S$, that is, the presently calculated pulse interval $I_{P(n)}$ could be abnormal, a determination is made in step a8 as to whether or not a heartbeat data reserve flag $F_R$, which will be described later, is set.

When it is determined in step a8 that the heartbeat data reserve flag $F_R$ is set, that is the previous determination is reserved because the previously calculated pulse interval $I_{P(n-1)}$ could be abnormal, processing proceeds to step a9, where the present pulse interval $I_{P(n)}$ is corrected to the sum of the present pulse interval $I_{P(n)}$ and the previous pulse interval $I_{P(n-1)}$, and a determination is made again in step a10 as to whether or not the corrected present pulse interval $I_{P(n)}$ is more than the reference pulse interval $I_{PB}$ subtracted by the subtraction time $T_S$ and less than the sum of the reference pulse interval IPB and the above additional time $T_A$. When it is determined in step a8 that the heartbeat data reserve flag $F_R$ is not set, that is, the previously calculated pulse interval $I_{P(n-1)}$ is normal and the present pulse interval $I_{P(n)}$ is abnormal, processing proceeds to step a11, where the heartbeat data reserve flag $F_R$ is set and, in step a12, a first input defect determination flag $F_{U1}$, a second input defect determination flag $F_{U2}$, and an input normal determination flag $F_{NI}$, which will be described later, are individually reset, and processing returns to step a1 following the next interrupt signal.

When it is determined in step a10 that the pulse interval $I_{P(n)}$ set in step a9 is more than the value of the reference pulse interval $I_{PB}$ subtracted by the preset subtraction time $T_S$ and less than the sum of the reference pulse interval $I_{PB}$ and the preset additional time $T_A$, that is, the previous pulse interval $I_{P(n-1)}$ is abnormal, processing proceeds to step a13, where the heartbeat data reserve flag $F_R$ is reset. A present heartbeat rate $R_{H(n)}$ is calculated in step a14 according to the pulse interval $I_{P(n)}$ corrected in step a9, and a determination is made in step a15 as to whether or not the heartbeat data timer has begun counting up, using the following equation:

$$R_{H(n)} = 60/I_{P(n)}.$$

When it is determined in step a15 that the heartbeat data timer has not begun counting up, counting up of the heartbeat data timer begins in step a16. the heartbeat data number $N_D$ is incremented by one in step a17, the pulse interval $I_{P(n)}$ set in step a9 is adopted as a new reference pulse interval $I_{PB}$ in step a18, and processing returns to step a1 following the above-described interrupt signal of the predetermined period.

On the other hand, when it is determined in step a6 that the pulse interval $I_{P(n)}$ is more than the sum of the reference pulse interval IPB and the preset additional time $T_A$, that is, a heartbeat pulse was expected between the previous time and the present time, processing proceeds to step a19, where the first input defect determination flag $F_{U1}$ is set, a determination is made in step a20 as to whether or not the input normal determination flag $F_{NI}$ described later is set, that is, the previous input is normal, processing proceeds to step 21, where the previously set pulse interval $I_{P(n)}$ is set as an initial -time of an input defect integrating timer, from which counting up is begun, and a determination is made in step a22 as to whether or not a count value $T_{CI}$ by the input defect integrating timer is longer than a preset time $T_{RI}$.

When it is determined in step a22 that the count value $T_{CI}$ of the input defect integrating timer is less than the above preset time $T_{RI}$, processing proceeds to step a1 after the above-described predetermined period interrupt signal. Further, when it is determined in step a22 that the count value $T_{CI}$ of the input defect integrating timer exceeds the preset time $T_{RI}$, that is, the heartbeat pulse data read in step a1 is due to continuous noise, the heartbeat data number $N_D$ is set to 0 in step a23, the count value $T_{CR}$ of the heartbeat data timer is reset to 0 in step a24, counting up of the input defect integrating timer is reset in step a25, and processing returns to step a1 following the predetermined period interrupt signal.

Further, when it is determined in step a20 that the input normal determination flag $F_{NI}$ is not set, that is, the previous input is abnormal, processing proceeds to step a26, where a determination is made as to whether or not the input defect integrating timer has begun counting up, when it is determined in step a26 that the input defect integrating timer has begun counting up, processing proceeds to the above step a22. On the contrary, when it is determined in step a22 that counting up has not begun by the input defect integrating timer, counting up of the input defect integrating timer begins in step a27, and processing returns to step a1 following the predetermined period interrupt signal.

When it is determined in step a10 that the pulse interval $I_{P(n)}$ set in step a9 is shorter than the value of the reference pulse interval $I_{PB}$ subtracted by the subtraction time $T_S$, or the pulse interval $I_{P(n)}$ is longer than the sum of the reference pulse interval IPB and the additional time $T_A$, that is, also the presently corrected pulse interval $I_{P(n)}$ is also abnormal, processing proceeds to step a28, where the second input defect determination flag $F_{U2}$ is set, and the first input defect determination flag $F_{U1}$, the input normal determination flag $F_{NI}$, and the heartbeat data reserve flag $F_R$ are individually reset in step a29, counting up of the input defect integrating timer begins in step a30, and processing returns to step a1 following the predetermined period interrupt signal.

Further, when it is determined in step a7 that the pulse interval $I_{P(n)}$ is longer than the value of the reference pulse interval $I_{PB}$ subtracted by the subtraction time $T_S$, that is, the presently calculated pulse interval $I_{P(n)}$ is normal, processing proceeds to step a31, where the normal input determination flag $F_{NI}$ used in the determination step of a20 is set, and a determination is made in step a32 as to whether or not the second input defect determination flag $F_{U2}$ is set. When it is determined in step a32 that the second input defect determination flag $F_{U2}$ is set, that is, abnormal heartbeat pulses are detected in two successive times, processing proceeds to step a33, where the count value $T_{CI}$ of the input defect integrating timer is reset to 0, the heartbeat data number $N_D$ is reset to 0 in step a34, the count value $T_{CR}$ of the heartbeat data timer is reset to 0 in step a35, and processing proceeds to step a14.

On the other hand, when it is determined in step a32 that the second input defect determination flag $F_{U2}$ is not set, processing proceeds to step a36, where a determination is made as to whether or not the first input defect determination flag $F_{U1}$ is set. When it is determined in step a36 that the first input defect determination flag $F_{U1}$ is set, that is, the previously calculated pulse interval $I_{P(n-1)}$ is too long compared to that previous calculations, processing proceeds to step a37, where a determination is made as to whether or not the count value $T_{CI}$ of the input defect integrating timer is greater than the preset time $T_{RI}$. When it is determined in step a36 that the first input defect determination flag $F_{U1}$ is not set, processing returns to step a14.

When it is expected in step a37 that the count value $T_{CI}$ of the input defect integrating timer is less than the preset time $T_{RI}$, that is, there was an undetected heartbeat pulse between the previous time and the time before previous time, a heartbeat data interpolation is made for the heartbeat pulse undetected between the previous time and the time before previous time, the first input defect determination flag $F_{U1}$ is reset in step a39, and processing returns to step a17.

When it is determined in step a37 that the count value $T_{CI}$ of the input defect integrating timer is longer than the preset time $T_{RI}$, that is, the previously calculated pulse interval $I_{P(n-1)}$ is abnormally long, since it is not a normal heartbeat pulse, processing proceeds to step a40, where the heartbeat data number $N_D$ is reset to 0, the count value $T_{CR}$ of the heartbeat data timer is reset to 0 in step a41, the count value $T_{CI}$ of the input defect integrating timer is reset to 0, and processing returns to step a1 following the predetermined period interrupt signal.

Heartbeat data calculated by these heartbeat processing means 13 and 14 should basically be the same but, when the heartbeat data differs for some reason, the signal selection means 15 adopts the one which outputs a greater heartbeat rate from the two heartbeat processing means 13 and 14 in view of control safety, and outputs it to the heartbeat processing means 18. Since the present embodiment employs two infrared heartbeat sensors 11 and 12, an exact heartbeat rate can be calculated even when the steering wheel 33 is gripped by only the right or left hand. In this case, it is natural to adopt the output from heartbeat processing means which outputs normal heartbeat data.

In the present embodiment, the heartbeat data processing means 18 calculates an average of heartbeat data of past four times (hereinafter referred to as "4-point running average heartbeat rate"), because there are 3 or 4 heartbeats during a respiration of one time in a rest, considering periodical changes in heartbeat in association with the driver's respiration, to remove fluctuations in heartbeat rate due to the driver's respiration. Further, from the 4-point running average heartbeat rates of the present time, previous time, and the time before previous time, calculation is made as to whether it is a peak point heartbeat rate in which the 4-point running average heartbeat rate of the previous time changes from an increasing tendency to a decreasing tendency, or from a decreasing tendency to an increasing tendency. Then, a gradient of adjacent peak point heartbeat rate obtained by dividing a deviation of adjacent peak point heartbeat rates by the time interval is calculated, and an average of heartbeat rate data of past 10 times (hereinafter referred to as "10-point running average heartbeat rate") and a simple average of heartbeat rate for past 30 seconds (hereinafter referred to as "30-sec average heartbeat rate") are calculated.

Figure 8:
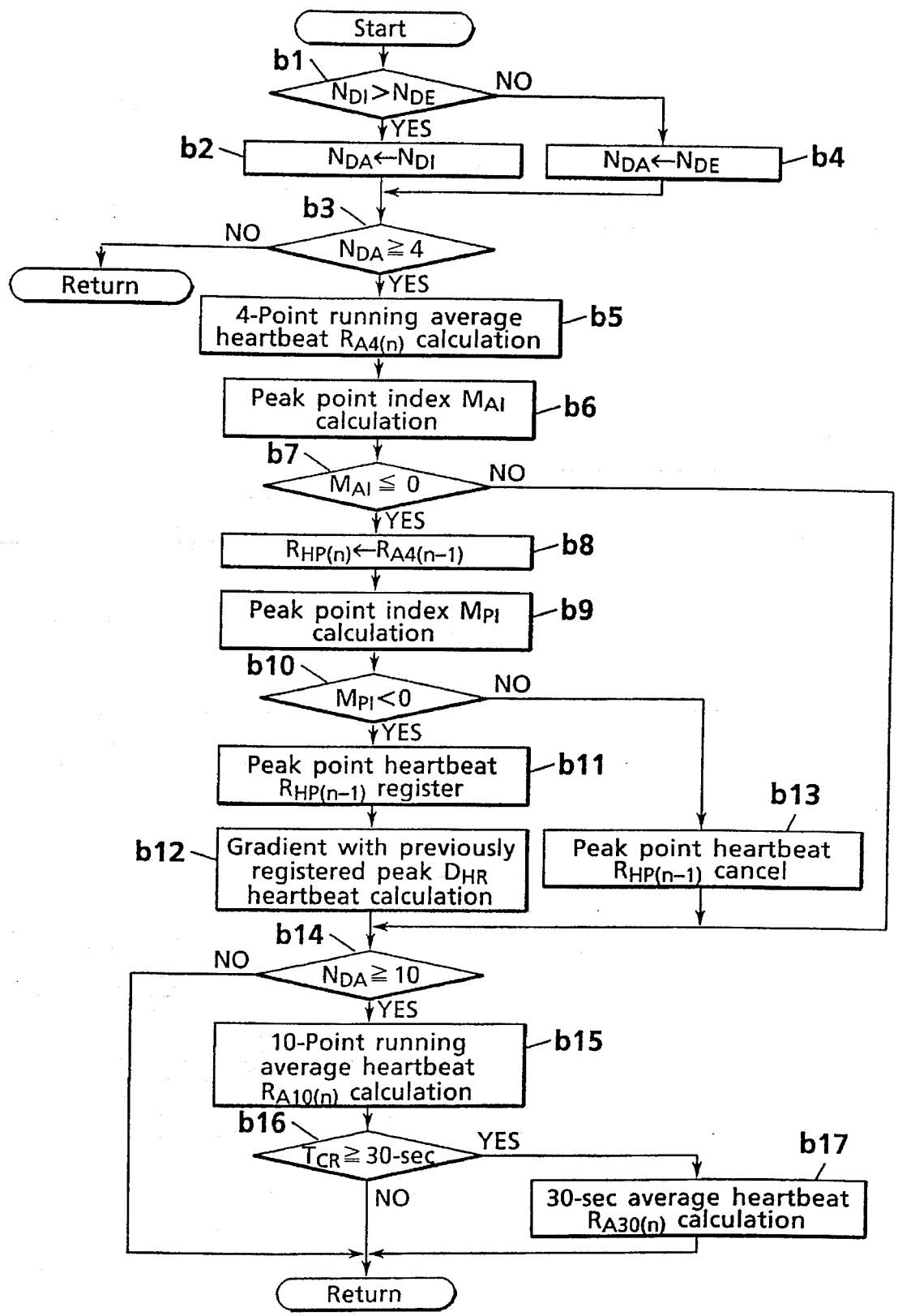
FIG. 8 is a flow chart showing processing performed by the heartbeat data processing means of the present embodiment.

Processing flow in the heartbeat data processing means 18 in the present embodiment is shown in FIG. 8. Specifically, a determination is made in step b1 as to whether or not the heartbeat data number $N_{DI}$ from the signal selection means 15 is more than the heartbeat data number $N_{DE}$ from the potential heartbeat sensor 16, and when it is determined in step b1 that the heartbeat data number $N_{DI}$ from the signal selection means 15 is more than the heartbeat data number $N_{DE}$ from the potential heartbeat sensor 16, processing proceeds to step b2, where the heartbeat data number $N_{DI}$ from one of the infrared heartbeat sensors 11 and 12 through the signal selection means 15 is adopted as an effective heartbeat data number $N_{DA}$, and a determination is made in step b3 as to whether or not the effective heartbeat data number $N_{DA}$ is more than 4 which is the number of data required for calculating a 4-point running average heartbeat rate $R_{A4}$. Further, when it is determined in step b1 that the heartbeat data number from the signal selection means 15 is less than the heartbeat data number $N_{DE}$ from the potential heartbeat sensor 16, processing proceeds to step b4, where the heartbeat data number $N_{DE}$ from the potential heartbeat sensor 16 is adopted as the effective heartbeat data number $N_{DA}$, and then processing proceeds to step b3.

When it is determined in step b3 that the effective heartbeat data number $N_{DA}$ is 4 or more, a 4-point running average heartbeat rate $R_{A4(n)}$ is calculated in step b5, a peak point index $M_{A1}$ of the 4-point running average heartbeat rate $R_{A4}$ is calculated using the equation recited below in step b6, and then a determination is made in step b7 as to whether or not the peak point index $M_{A1}$ is 0 or less. When it is determined in step b3 that the effective heartbeat data number $N_{DA}$ is less than 4, since the 4-point running average heartbeat rate $R_{A4(n)}$ cannot be calculated in step b5, processing returns to step b1.

$$M_{AI} = \{R_{A4(n)} - R_{A4(n-1)}\} \cdot \{R_{A4(n-1)} - R_{A4(n-2)}\}.$$

When it is determined in step b7 that the peak point index $M_{AI}$ is less than 0, that is, the values are the same only at the present time and the previous time, or the same only at the previous time and at the time before the previous time, or the previous 4-point running average heartbeat rate $R_{A4(n-1)}$ is greater than the present one and the previous one is greater than the 4-point running average heartbeat rate $R_{A4(n-2)}$ at the time before previous time, or the present one is greater than the previous 4-point running average heartbeat rate $R_{A4(n-1)}$ and the 4-point running average heartbeat rate $R_{A4(n-2)}$ at the time before previous time, processing proceeds to step b8, where the previous 4-point running average heartbeat rate $R_{A4(n-1)}$ is temporarily adopted as a peak point heartbeat rate $R_{HP(n)}$, a peak point index $M_{PI}$ of a peak point heartbeat rate $R_{HP}$ is calculated using the equation recited below, and a determination is made in step b10 as to whether or not the peak point index $M_{PI}$ is less than 0:

Ti $M_{P1} = \{R_{HP(n)} - R_{HP(n-1)}\} \cdot \{R_{HP(n-1)} - R_{HP(n-2)}\}.$

When it is determined in step b10 that the peak point index $M_{P1}$ is smaller than 0, that is, the previous peak point heartbeat rate $R_{HP(n-1)}$ is greater or smaller than the present peak point heartbeat rate $R_{HP(n)}$ and the peak point heartbeat rate $R_{HP(n-2)}$ at the time before the previous time, processing proceeds to step b11, where the previous peak point heartbeat rate $R_{HP(n-1)}$ is registered, a gradient $D_{RH}$ is obtained by dividing a difference between the previously registered peak point heartbeat rate $R_{HP(n-2)}$ and the presently registered peak point heartbeat rate $R_{HP(n-1)}$ by this time is calculated in step b12, and a determination is made in step b13 as to whether or not the effective heartbeat data number $N_{DA}$ is 10 or more which is the number required for calculating a 10-point running average heartbeat rate $R_{A10}$. That is, when it is determined in step b10 that the peak point index $M_{PI}$ is 0 or more, that is, the previous peak point heartbeat rate $R_{HP(n-1)}$ is the same as the present time or the time before the previous time, or the magnitudes of the peak point heartbeat rates $R_{HP}$ are in the order of present time, previous time, and the time before previous time, processing proceeds to step b13, where the previous peak point heartbeat rate $R_{HP(n-1)}$ is not registered but reset, and then processing proceeds to step b14. Also, when it is determined in step b7 that the peak point index $M_{AI}$ exceeds 0, that is, if the magnitudes of the peak point heartbeat rates $R_{HP}$ are in the order of present time, previous time, and the time before previous time, then the previous 4-point running average heartbeat rate $R_{A4(n-1)}$ is not a peak point heartbeat rate, and processing proceeds to step b14.

When it is determined in step b14 that the effective heartbeat data number $N_{DA}$ is 10 or more, the 10-point running average heartbeat rate $R_{A10(n)}$ is calculated in step b15, and a determination is made in step b16 as to whether or not the count value $T_{CR}$ of the heartbeat timer is 30 seconds or more. When it is determined in step b13 that the effective heartbeat data number $N_{DA}$ is less than 10, since the 10-point running average heartbeat rate $R_{A10(n)}$ cannot be calculated in step b15, the processing returns to step b3.

When it is determined in step b16 that the count value $T_{CR}$ of the heartbeat data timer is 30 seconds or more, the 30-sec average heartbeat rate $R_{A30(n)}$ is calculated in step b17, and processing returns to step b1. When it is determined that the counter value $T_{CR}$ of the heartbeat data timer is less than 30 seconds, that is, the 30-sec average heartbeat rate $R_{A30(n)}$ cannot be calculated, the processing returns again to step b1.

The heartbeat awareness determination means 19 determines whether a variation in a heartbeat rate calculated by the heartbeat data processing means 18 is stable, that is, a variation width of the 4-point running average heartbeat rate within 30 seconds falls within 2, for example, and represents an area of stable awareness of the driver as shown in FIG. 3(4), the 30-sec average heartbeat rate $R_{A30}$ in the area of stable awareness calculated as a reference heartbeat rate and, when the peak point heartbeat rate $R_{HP}$ calculated by the heartbeat data processing means 18 is slightly smaller than the reference heartbeat rate after the driver is determined to be in the area of stable awareness, the driver is determined to be in a transition area in FIG. 3(5), and then the reference heartbeat rate and the present heartbeat data of the driver are compared to determine the awareness of the driver, setting a warning level corresponding to the driver's level of awareness.

Figure 9:
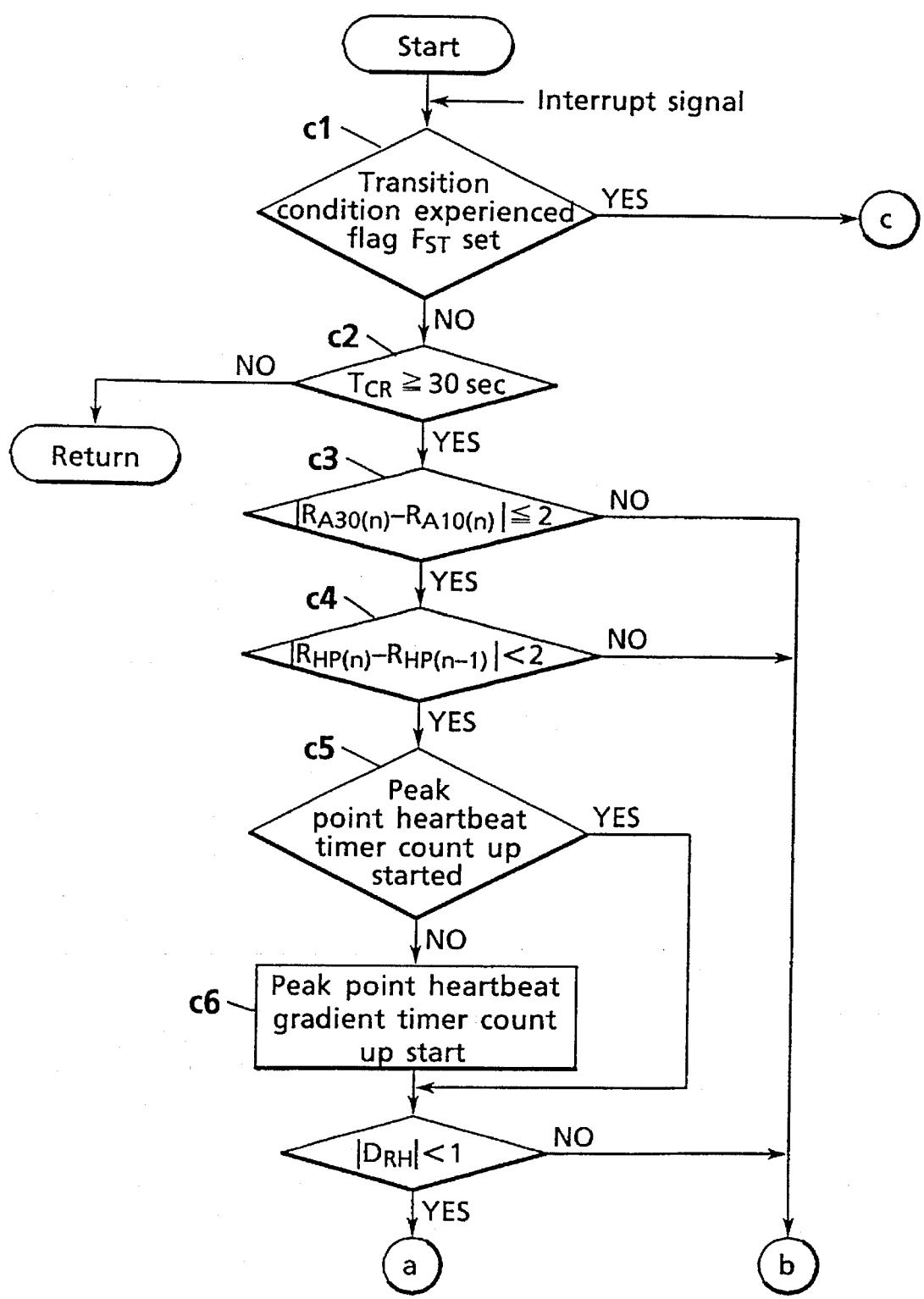
FIG. 9 is a flow chart showing processing performed by the heartbeat awareness determination means of the present embodiment along with FIGS. 10 and 11.
Figure 10:
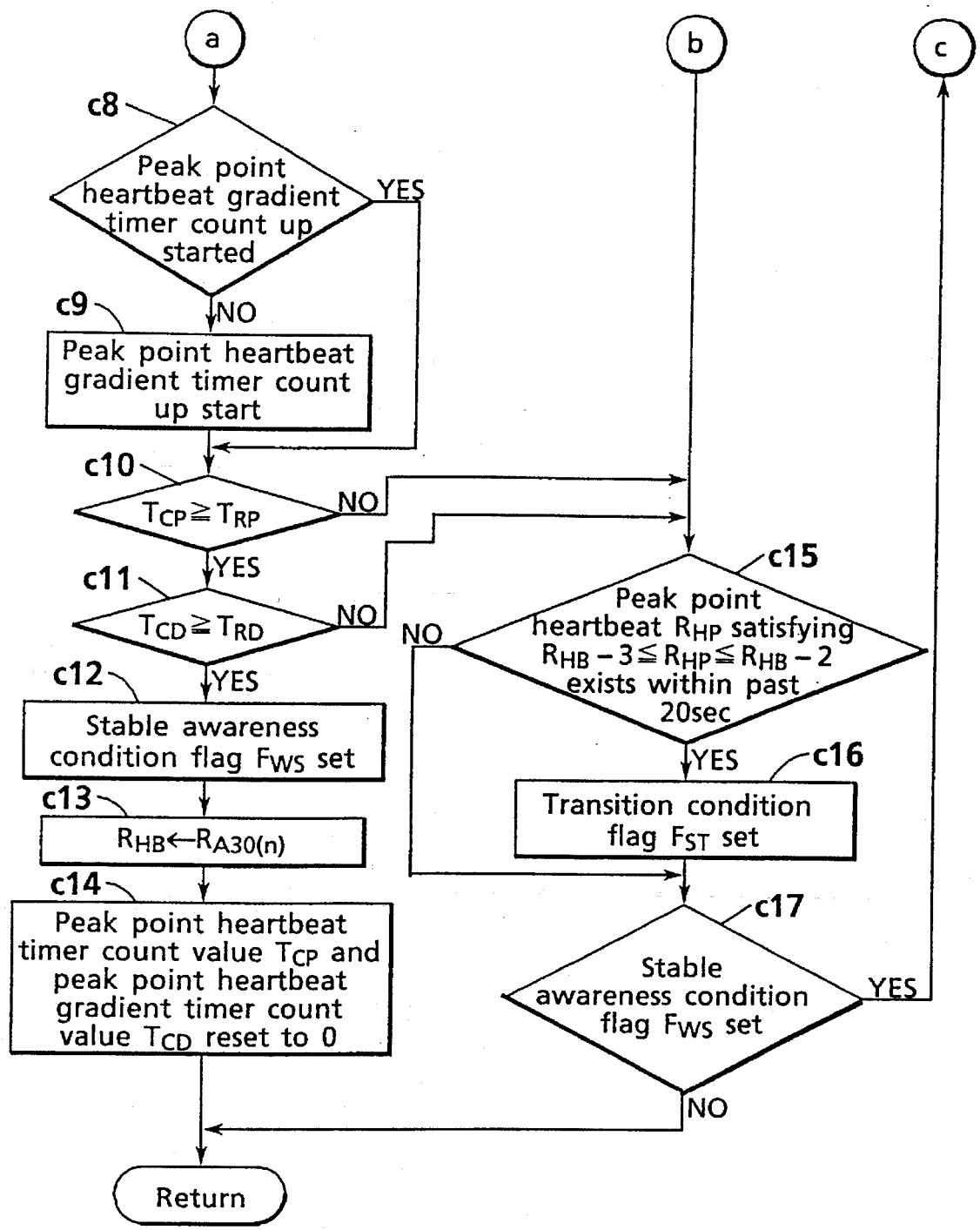
FIG. 10 is a flow chart showing processing performed by the heartbeat awareness determination means of the present embodiment along with FIGS. 9 and 11.
Figure 11:
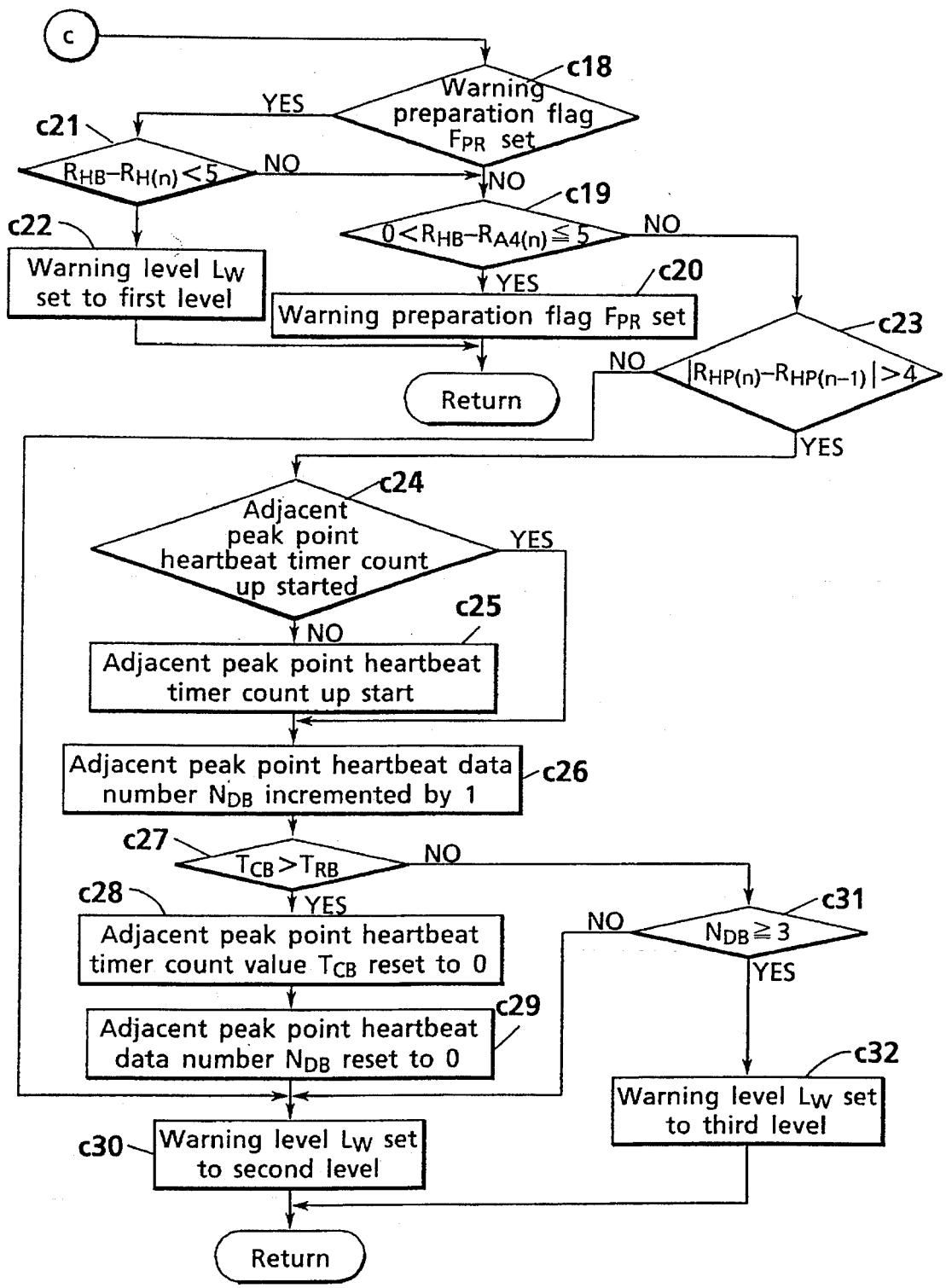
FIG. 11 is a flow chart showing processing performed by the heartbeat awareness determination means of the present embodiment along with FIGS. 9 and 10.

The processing flow of the heartbeat awareness determination means 19 in the present embodiment is shown in FIGS. 9 to 11. Specifically, in the present embodiment, processing by the heartbeat awareness determination means 19 is carried out in a predetermined period, for example, at every interrupt signal of 15 msec. First, a determination is made in step c1 as to whether or not a transition condition experienced flag $F_{SI}$ is set, however, since the transition condition experienced flag $F_{SI}$ is not set at the beginning, processing proceeds to step c2, where a determination is made in step c2 as to whether or not the count value $T_{CR}$ of the heartbeat data timer is 30 seconds or more. When it is determined in step c2 that the count value $T_{CR}$ of the heartbeat data timer is 30 seconds or more, that is, the heartbeat data is normal over a period of 30 seconds or more, the processing proceeds to step c3, where a determination is made as to whether or not an absolute value of the 30-sec average heartbeat rate $R_{A30(n)}$ subtracted by the 10-point running average heartbeat rate $R_{A10(n)}$ is 2 or less. When it is determined in step c2 that the count value $T_{CR}$ of the heartbeat data timer is shorter than 30 seconds, that is, the 10-point running average heartbeat rate $R_{A10(n)}$ cannot be calculated, the processing returns to step c1 and step c1 is repeated according to the next interrupt signal.

When it is determined in step c3 that the absolute value of the 30-sec average heartbeat rate $R_{A30(n)}$ subtracted by the 10-point running average heartbeat rate $R_{A10(n)}$ is 2 or less, that is, the heartbeat rate of the driver has almost no variation, a determination is made in step c4 as to whether or not the present peak point heartbeat rate $R_{HP(n)}$ subtracted by the previous peak point heartbeat rate $R_{HP(n-1)}$ is less than 2. When it is determined in step c4 that the absolute value of the present peak point heartbeat rate $R_{HP(n)}$ subtracted by the previous peak point heartbeat rate $R_{HP(n-1)}$ is less than 2, that is, a variation in the peak point heartbeat rate $R_{HP}$ is relatively moderate, a determination is made in step c5 as to whether or not the peak point heartbeat timer has begun counting up. In this case, since counting up of the peak point heartbeat timer has not begun, the processing proceeds to step c6, where counting up of the peak point heartbeat timer is begun, and a determination is made in step c7 as to whether or not the absolute value of a gradient $D_{RH}$ of the present peak point heartbeat rate $R_{HP(n)}$ and the previous peak point heartbeat rate $R_{HPn-1)}$ is less than 1. Also, when it is determined in step c5 that the peak point heartbeat timer has begun counting up, the processing proceeds to step c7.

When it is determined in step c7 that the absolute value of gradient $D_{RH}$ of the adjacent peak point heartbeat rate $R_{HP}$ is less than 1, that is, the peak point heartbeat rate $R_{HP}$ is increasing or decreasing slightly, the processing proceeds to step c8, where a determination is made as to whether or not a peak point heartbeat gradient timer has begun counting up. In this case, the peak point heartbeat gradient timer does not begin counting up and the processing proceeds to step c9, where the peak point heartbeat timer begins to count up, and a determination is made in step c10 as to whether or not the count value $T_{CP}$ of the peak point heartbeat timer is a predetermined time $T_{RP}$, for example, 30 seconds, or more. Also, when it is determined in step c8 that the peak point heartbeat gradient timer has begun counting up, the processing proceeds to step c10.

When it is determined in step c10 that the count value $T_{CP}$ of the peak point heartbeat timer is the preset time $T_{RP}$ or more, that is, a condition where the variation width of peak point heartbeat rate has continued for a long time, a determination is made in step c11 as to whether or not the count value $T_{CP}$ of the peak point heartbeat gradient timer is the preset time $T_{RP}$, for example, 30 seconds, or more.

When it is determined in step c11 that the count value $T_{CP}$ of the peak point heartbeat gradient timer is more than the preset time $T_{RP}$, that is, a condition where the peak point heartbeat rate increasing or decreasing slightly has continued for a long time, a stable awareness condition experienced flag $F_{WS}$ is set in step c12, the 30-sec average heartbeat rate $R_{A30(n)}$ is adopted as a reference heartbeat rate $R_{HB}$, the count value $T_{CP}$ of the peak point heartbeat timer and the count value $T_{CD}$ of the peak point heartbeat gradient timer are individually reset to 0 in step c14, and the processing returns to step c1 according to the next interrupt signal.

Further, when it is determined in step c3 that the absolute value of the 30-sec average heartbeat rate $R_{A30(n)}$ subtracted by the 10-point running average heartbeat rate $R_{A10(n)}$ exceeds 2, that is, the change in heartbeat rate of the driver is relatively large, or when it is determined in step c4 that absolute value of the present peak point heartbeat rate $R_{HP(n)}$ subtracted by the previous peak point heartbeat rate $R_{HP(n-1)}$ is 2 or more, that is, the peak point heartbeat rate $R_{HP}$ increases or decreases relatively sharply, or when it is determined in step c7 that the absolute value of gradient $D_{RH}$ of the peak point heartbeat rate $R_{HP}$ is 1 or more, that is, the peak point heartbeat rate $R_{HP}$ increases or decreases relatively sharply, or when it is determined in step c10 that the count value $T_{CP}$ of the peak point heartbeat timer does not reach the preset time $T_{RP}$, that is, a small variation in the peak point heartbeat rate does not continue for a long time, or when it is determined in step c11 that the count value $T_{CD}$ of the peak point heartbeat gradient timer does not reach the preset time $T_{RD}$, that is, a condition where the peak point heartbeat rate increases or decreases very slightly does not continue for a long time, the processing proceeds to step c15, where a determination is made as to whether or not there was a peak point heartbeat rate $R_{HP}$ not smaller than the value of the reference heartbeat rate $R_{HB}$ subtracted by 3 and greater than the reference heartbeat rate $R_{HB}$ subtracted by 2 in the past 20 seconds.

When it is determined in step c15 that there was a peak point heartbeat rate $R_{HP}$ not smaller than the value of the reference heartbeat rate $R_{HB}$ subtracted by 3 and greater than the reference heartbeat rate $R_{HB}$ subtracted by 2 in the past 20 seconds, that is the driver has entered the transition area, the processing proceeds to step c16, where a transition condition flag $F_{ST}$ is set, and a determination is made in step c17 as to whether or not the stable awareness condition flag $F_{WS}$ is set. When it is determined in step c15 that there was not a peak point heartbeat rate $R_{HP}$ not smaller than the value of the reference heartbeat rate $R_{HB}$ subtracted by 3 and greater than the reference heartbeat rate $R_{HB}$ subtracted by 2 in the past 20 seconds, that is, the driver has not entered the transition area, the processing proceeds to step c17, and when it is determined in step c17 that the stable awareness condition flag $F_{WS}$ is not set, the processing returns to step c1 according to the next interrupt signal.

On the other hand, when it is determined in step c16 that the transition condition flag $F_{ST}$ is set, or when it is determined in step c17 that the stable awareness condition flag $F_{WS}$ is set, a determination is made in step c18 as to whether or not a warning preparation flag $F_{PR}$ described later is set. Since the warning preparation flag $F_{PR}$ is not set at the beginning, the processing proceeds to step c19, where a determination is made as to whether or not the value of the reference heartbeat rate $R_{HB}$ subtracted by the present 4-point running average heartbeat rate $R_{A4(n)}$ exceeds 0 and is less than or equal to 5. When it is determined in step c19 that the value of the reference heartbeat rate $R_{HB}$ subtracted by the present 4-point running average heartbeat rate $R_{A4(n)}$ exceeds 0 and less than or equal to 5, that is, the awareness of the driver tends to decrease, the warning preparation flag $F_{PR}$ is set in step c20, and the step of c1 and after is repeated according to the next interrupt signal.

When it is determined in step c18 that the warning preparation flag $F_{PR}$ is set, that is, the awareness of the driver tends to decrease, the processing proceeds to step c21, where a determination is made as to whether or not the value of the reference heartbeat rate $R_{HB}$ subtracted by the present heartbeat rate $R_{H(n)}$ is less than 5. When it is determined in step c21 that the value of the reference heartbeat rate $R_{HB}$ subtracted by the present heartbeat rate $R_{H(n)}$ is less than 5, that is, the decrease in heartbeat rate is relatively small, the processing proceeds to step c22, where the warning level $L_W$ is set to the first level, and the processing returns to step c1 according to the next interrupt signal. When it is determined in step c21 that the value of the reference heartbeat rate $R_{HB}$ subtracted by the present heartbeat rate $R_{H(n)}$ is 5 or more, that is, the decrease in heartbeat rate is relatively large, the processing proceeds to step c19. When it is determined in step c19 that the value of the reference heartbeat rate $R_{HB}$ subtracted by the present 4-point running average heartbeat rate $R_{A4(n)}$ is greater than 5, that is, the decrease in heartbeat rate of the driver is very large, the processing proceeds to step c23, where a determination is made as to whether or not the absolute value of the present peak point heartbeat rate $R_{HP(n)}$ subtracted by the previous peak point heartbeat rate $R_{HP(n-1)}$ is greater than 4.

When it is determined in step c23 that the absolute value of the present peak point heartbeat rate $R_{HP(n)}$ subtracted by the previous peak point heartbeat rate $R_{HP(n-1)}$ is greater than 4, that is, the driver is quickly becoming less aware, the processing proceeds to step c24, where a determination is made as to whether or not the adjacent peak point heartbeat timer has begun counting up. When it is determined that the adjacent peak point heartbeat timer has not begun counting up, the adjacent peak point heartbeat timer begins counting up in step c25, the adjacent peak point data number $N_{DB}$ is increased by 1 in step c26, and a determination is made in step c27 as to whether or not the count value $T_{CB}$ of the adjacent peak point heartbeat timer exceeds a preset time $T_{RB}$, for example, 20 seconds. When it is determined in step c24 that the adjacent peak point heartbeat timer has begun counting up, the processing proceeds to step c26.

When it is determined in step c27 that the count value $T_{CB}$ of the adjacent peak point heartbeat timer exceeds the preset time $T_{RB}$, that is, the driver's heartbeat rate varies to a large extent, the processing proceeds to step c28, where the count value $T_{CB}$ of the adjacent peak point heartbeat timer is reset to 0, the adjacent peak point heartbeat data number $N_{DB}$ is also rest to 0 in step 29, the warning level is set to the second level in step c30, and the processing returns to step c1 according to the next interrupt signal. When it is determined in step c23 that the absolute value of the present peak point heartbeat rate $R_{HP(n)}$ subtracted by the previous peak point heartbeat rate $R_{HP(n-1)}$ is 4 or less, that is, the driver's awareness continues to decrease, the processing proceeds to step c30, where the warning level is set to the second level.

Further, when it is determined in step c27 that the count value $T_{CB}$ of the adjacent peak point heartbeat timer is the preset time $T_{RB}$ or less, that is, large variations in the driver's heartbeat rate do not continue for a long time, the processing proceeds to step c31, where a determination is made as to whether or not the adjacent peak point heartbeat data number $N_{DB}$ is more than 3. When it is determined that the adjacent peak point heartbeat data number $N_{DB}$ is more than 3, that is, the driver's awareness periodically decreases, the processing proceeds to step c32, where the warning level is set to the third level, and the processing returns to step c1 according to the next interrupt signal. When it is determined in step c31 that the adjacent peak point heartbeat data number $N_{DB}$ is less than 3, that is, the driver's awareness is not periodically decreasing, the processing proceeds to step c30.

In order to drive the vehicle exactly according to the road shape, the driver coarsely steers the steering wheel 33 according to curves in the road, and more finely steers the vehicle according to the road condition. That is, to drive on the road from the present position of the driver to a target position, the steering wheel 33 is coarsely controlled according to the road shape and, when the driver controls the vehicle according to the road condition, the steering wheel 33 is finely steered according to the position of the vehicle relative to the road every moment. The fine steering of the steering wheel 33 can be detected to determine the awareness of the driver.

Figure 12:
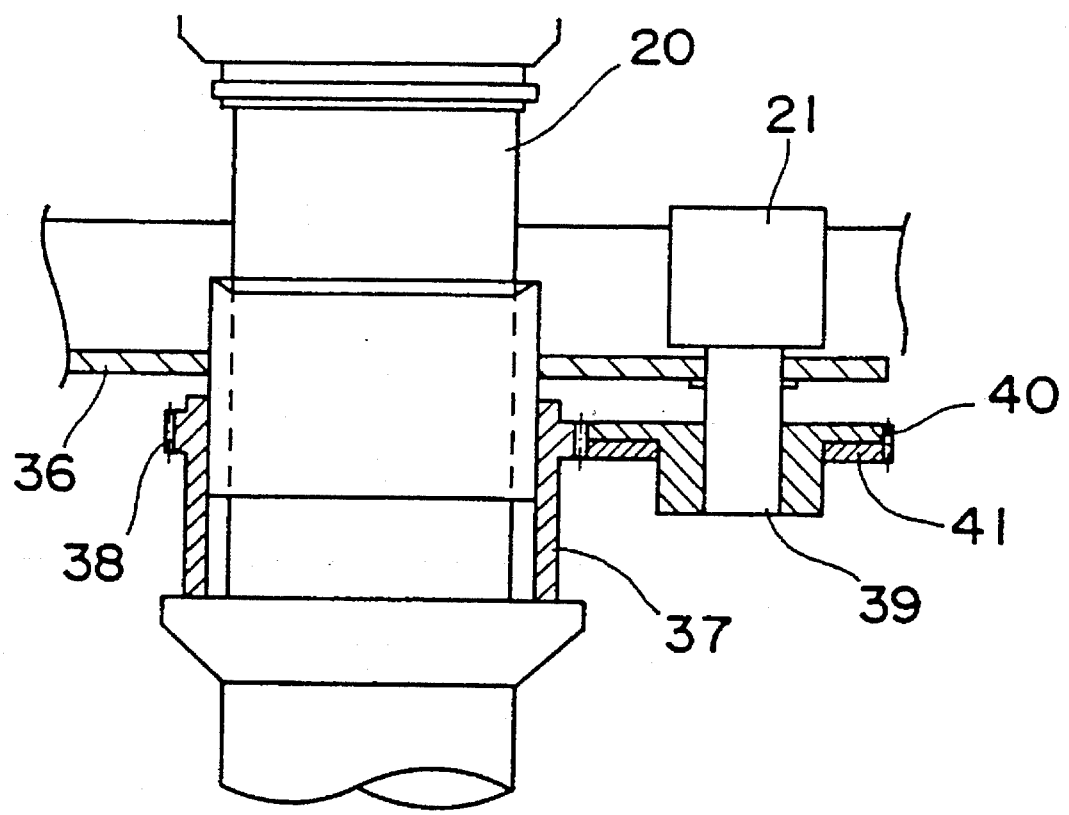
FIG. 12 is a schematic enlarged view showing part of the steering shaft to which the steering angle sensor is mounted.

FIG. 12 illustrates an enlarged cross-sectional structure of the steering shaft 20 to which the steering angle sensor 21 is mounted. The steering shaft 20, provided integrally with the steering wheel 93, is rotatably mounted on a steering column 36, the steering shaft 20 is provided with a gear cylinder 37 integrally and coaxially, and the gear cylinder 37 is integrally formed with a drive gear The steering column 36 is provided adjacent to the steering shaft 20 with the steering angle sensor 21, which is a potentiometer, a rotary shaft 39 of the steering angle sensor 21 is provided integrally with a drive gear 40 and engaged with a backlash removing gear 41 which is rotatable relative to the drive gear 40. The drive gear 38 of the gear cylinder 37 engages with the drive gear 40 and the backlash removing gear 41.

Therefore, when the steering wheel 33 is operated, the steering shaft 20 rotates accordingly, and the drive gear 40 is rotated by the backlash removing gear 41 of which the phase relative to the drive gear 40 is previously adjusted. Rotation exactly corresponding to the turning of the steering shaft 20 is transmitted to the rotary shaft 39 of the steering angle sensor 21. A turning condition of the steering shaft 20 is exactly detected by the steering angle sensor, which is output as an electrical signal.

The vehicle speed sensor 24 detects rotation of the output shaft of the transmission (not shown in the present embodiment), however, it is possible to employ other known types of vehicle sensors which detect the vehicle speed according to the rotation speed of the driven wheels.

The steering angle data processing means 22 calculates a standard value of the steering component which is frequency analyzed to determine the awareness of the driver according to detection signals from the steering angle sensor 21 and the vehicle speed sensor 24, and processes the absolute value of the detection signal of the steering angle sensor 21, which is bandpass filtered using a running average equation to obtain steering angle data. Specifically, the steering angle data is sequentially received every 0.1 sec with a sampling frequency of 10 Hz. The steering angle data is FFT (Fast Fourier Transform) analyzed to obtain magnitudes (power spectrum) of components of individual frequency bands.

Figure 13:
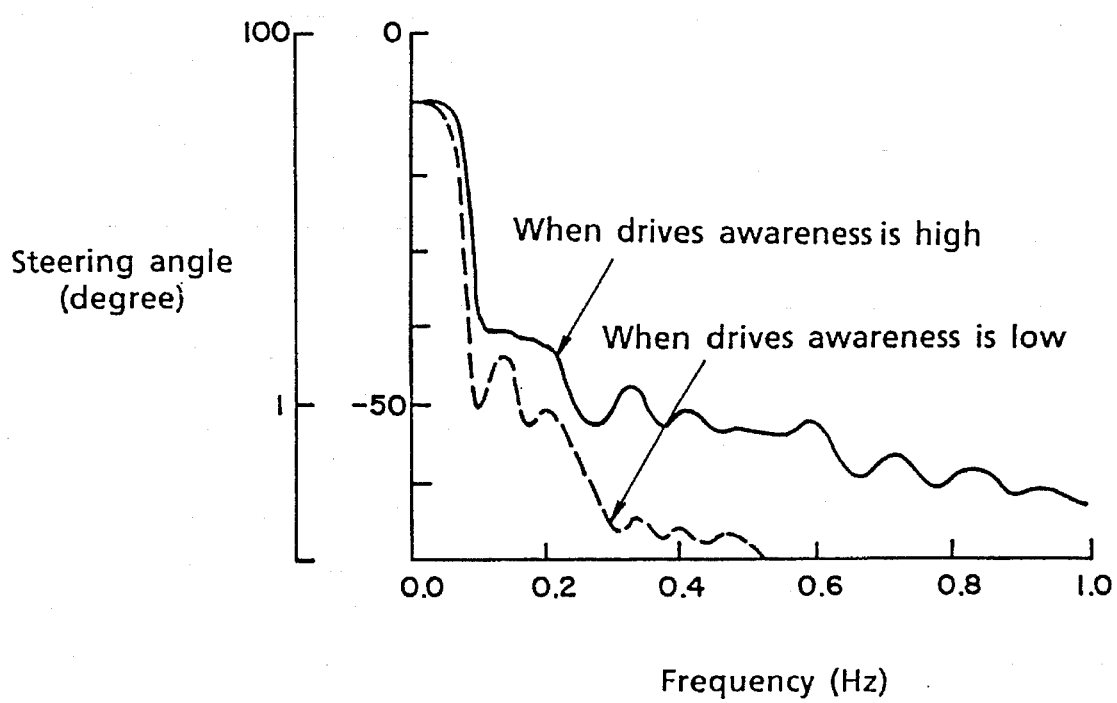
FIG. 13 is a graph showing a visual steering component of the driver versus steering angle frequency distribution of the steering wheel.
Figure 14:
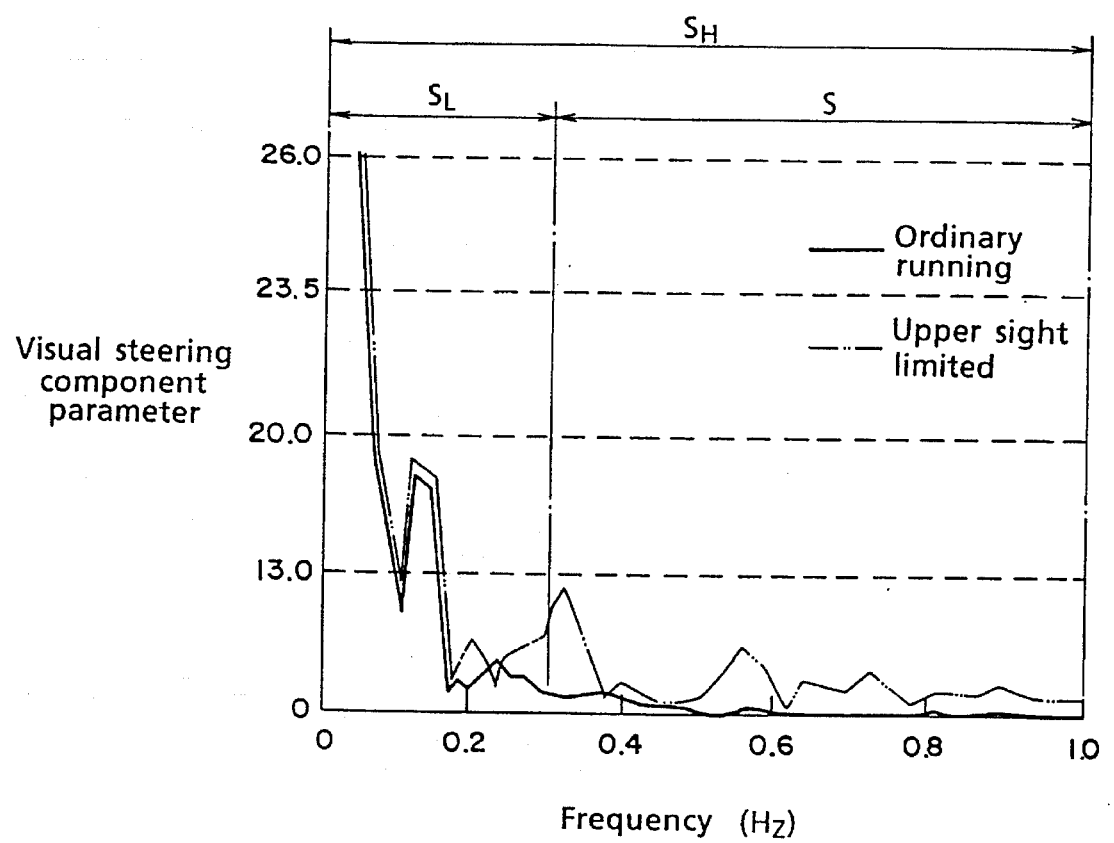
FIG. 14 is a graph showing a steering angle frequency distribution of the steering wheel when an upward sight limitation is placed on the driver.

FIG. 13 is a graph showing the obtained frequency distribution of steering angle signal of the steering wheel 33 vs, motion characteristics of the driver, in which the solid lines indicate an ordinary driver with high awareness, and the broken lines indicate the driver with decreased awareness. In the graph, 1 Hz means 1 turn per second of the steering wheel 33, 0.1 Hz means 1 turn per 10 seconds of the steering wheel 33, and 0.5 Hz means 1 turn per 2 seconds of the steering wheel 33. As can be seen from the graph, the frequency of fine manipulation of the steering wheel 33 increases with increasing driver awareness, and the frequency of fine manipulation of the steering wheel 33 decreases with decreasing driver awareness. Therefore, it is possible to determine the awareness of the driver by detecting only the area of fine manipulation of the steering wheel 33 and comparing it with a preset reference value.

That is, detection data is divided into predetermined frequency bands by determining an average value of a plurality of points of every sampling period from the present to the past by a low-pass filter of less than a predetermined frequency, that is, by running average calculation. Specifically, from the graph shown in FIG. 13, the 0.3–1.0 Hz component of fine manipulation of the steering wheel 33 is set as an area of visual steering component (hereinafter referred to as "visual steering component"), a component of less than 0.3 Hz is cut off because this area represents coarse manipulation of the steering wheel 33 according to curves in the road, and a component of more than 1.0 Hz is also cut off.

The above visual steering component will be described later in detail.

Division into frequency bands is achieved by a running average calculation. In general, where a sampling interval is $I_S$, and a cut-off frequency is f, the number M of the samples to be average can be determined by the equation shown below:

$$M=0.443/(I_S \cdot f).$$

Therefore, to determine a steering component area $S_H$ of less than 1.0 Hz, a number $M_H$ of samples when the cut-off frequency is 1.0 Hz is calculated.

$$M_H=0.448/(0.1 \times 1.0).$$

Further, to determine a steering component area $S_L$ of greater than 0.3 Hz, a number $M_L$ of samples when the cut-off frequency is 0.3 Hz is calculated.

$$M_L=0.443/(0.1 \times 0.3).$$

Thus, the numbers for dividing the visual steering area S are calculated as $M_H=4$ and $M_L=15$.

Therefore, a 4-point running average steering angle $P_{A4}$ and a 15-point running average steering angle $P_{A15}$ of every sampling period from the present and past are calculated and, since the 1 second and 7 seconds, that is, the sampling periods are 0.1 second, a 10-point running average of the 4-point running average visual steering angle $P_{A4}$ (hereinafter referred to as "10×4 point running average steering angle") $P_{A4-10}$, a 70-point running average (hereinafter referred to as "70×4 point running average steering angle") $P_{A4-70}$, a 10-point running average of the 15-point running average steering angle (hereinafter referred to as "10×15 point running average steering angle") $P_{A15-10}$, and a 70-point running average (hereinafter referred to as "70×15 point running average steering angle") $P_{A15-70}$ are calculated. By determining the differences of these values, parameters $P_{S10}$ and $P_{S70}$ in the visual steering component area S can be calculated.

In the present embodiment, when preparing the graph showing the visual steering component of the driver vs. the frequency distribution of steering angle signal of the steering wheel 33 shown in FIG. 13, a predetermined traveling test is carried out to determine the visual steering component of an aware driver during ordinary traveling (solid lines) and the visual steering component of an unaware (asleep) driver (broken lines).

In general, a driver manipulates the steering wheel 33 to trace the traveling lane of the road or his target course in view of the traveling speed based on visual information of "road shape in front of the vehicle" and "present position of the vehicle on the road". The present inventors discovered that when part of the visual information is limited, the limitation of visual information affects the operation characteristics of the steering wheel 33. That is, visual steering is controlled mainly by limitation of the driver's visual information, traveling speed, and individual differences on the steering angle frequency response of the steering wheel 33. This was announced at the "Dynamic and Design Conference 1992" of the Society of Mechanical Engineering on Jul. 7–8, 1992, of which test results are briefly described below.

Figure 15:
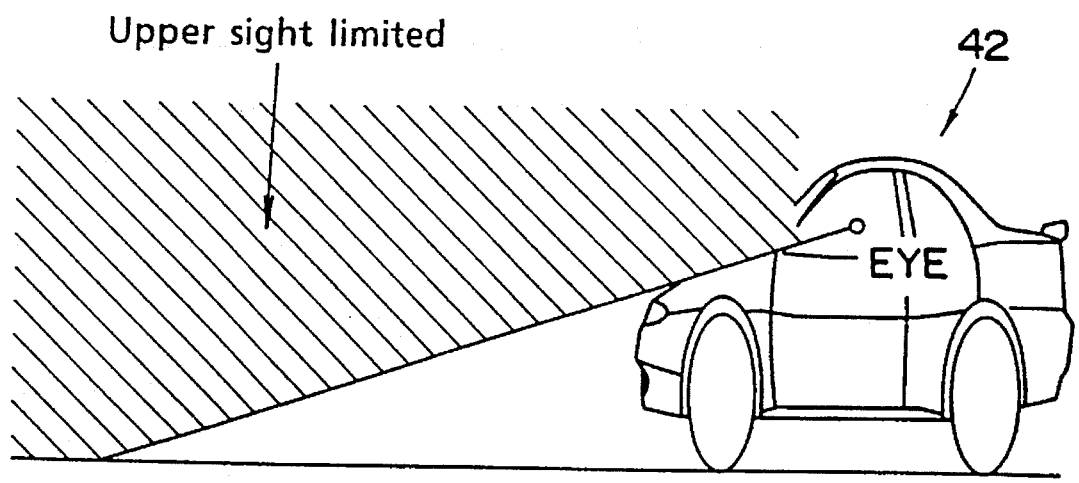
FIG. 15 is a schematic view illustrating an upward sight limitation is on the driver.

In tests conducted to determine the operation characteristics of the steering wheel 33 by the driver, using a predetermined curved road, the vehicle traveled at a predetermined speed with part of the driver's masked. Specifically, as shown in FIG. 15, a traveling test was carried out with the driver's forward sight at a predetermined distance of a vehicle 42, and steering angle data of the steering wheel 33 was frequency analyzed to determine the operation characteristics. As a result, when ordinary traveling and traveling with limited upward sight were frequency analyzed, a conspicuous difference was noted between both cases in the range from 0.3 to 1.0 Hz. It can be estimated from the result that the data of the 0.3–1.0 Hz area proves accurate feedback correction steering control of the positional relation between the vehicle 42 and the road in front of-the vehicle 42.

Since the driver's upward sight was limited in this test, the visual steering component was more apparent than during ordinary traveling.

Therefore, the fine steering component of the steering wheel 33, that is, the visual steering component can be detected by frequency analyzing steering angle data of the steering wheel 33, and extracting data of the 0.3–1.0 Hz area. Further, as can be seen from the fact that the result agrees with the tendency of the graph shown in FIG. 13, the level of awareness of the driver can be determined from data of the visual steering component area.

Figure 16:
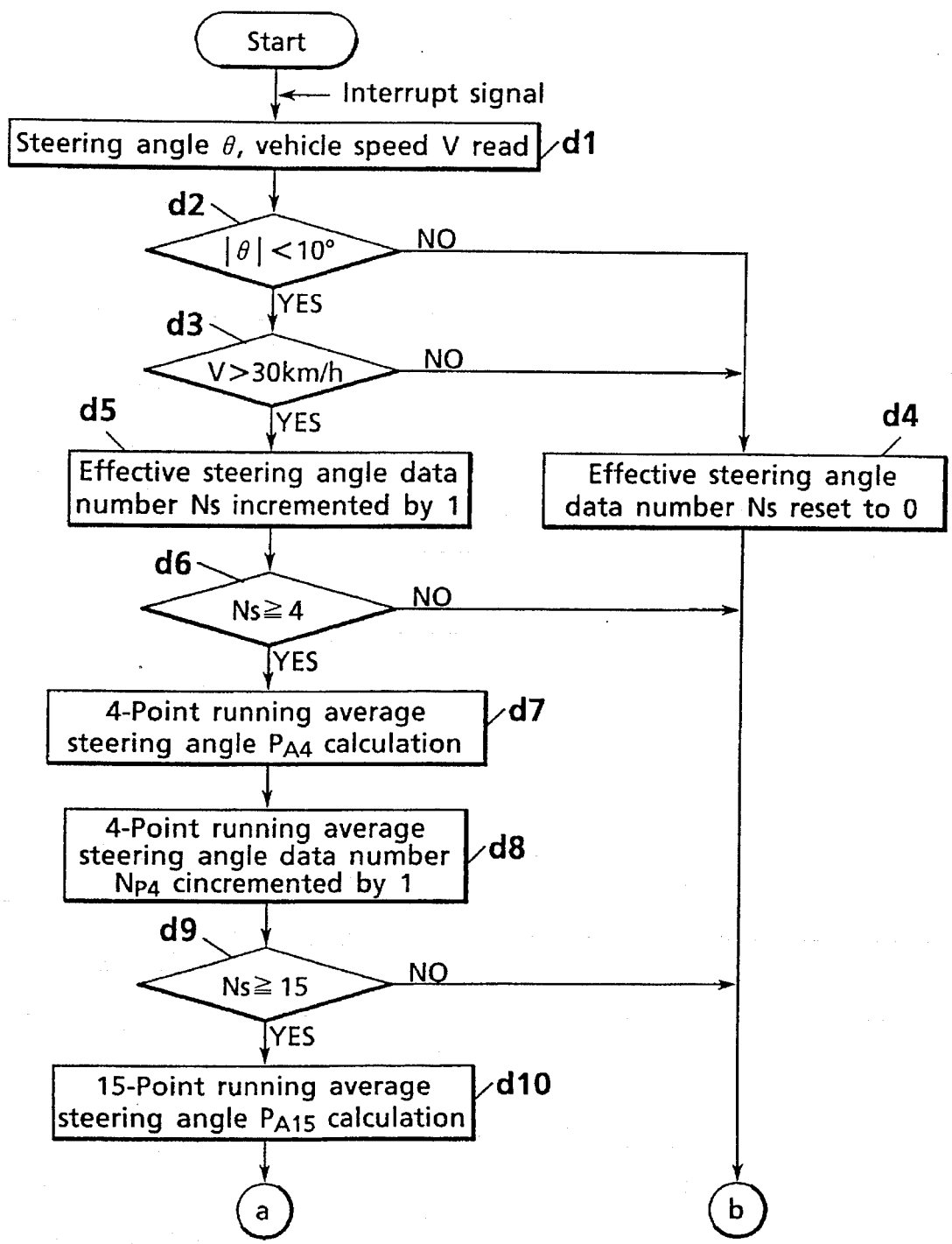
FIG. 16 is a flow chart showing processing performed by the steering angle data processing means of the present embodiment along with FIG. 17.
Figure 17:
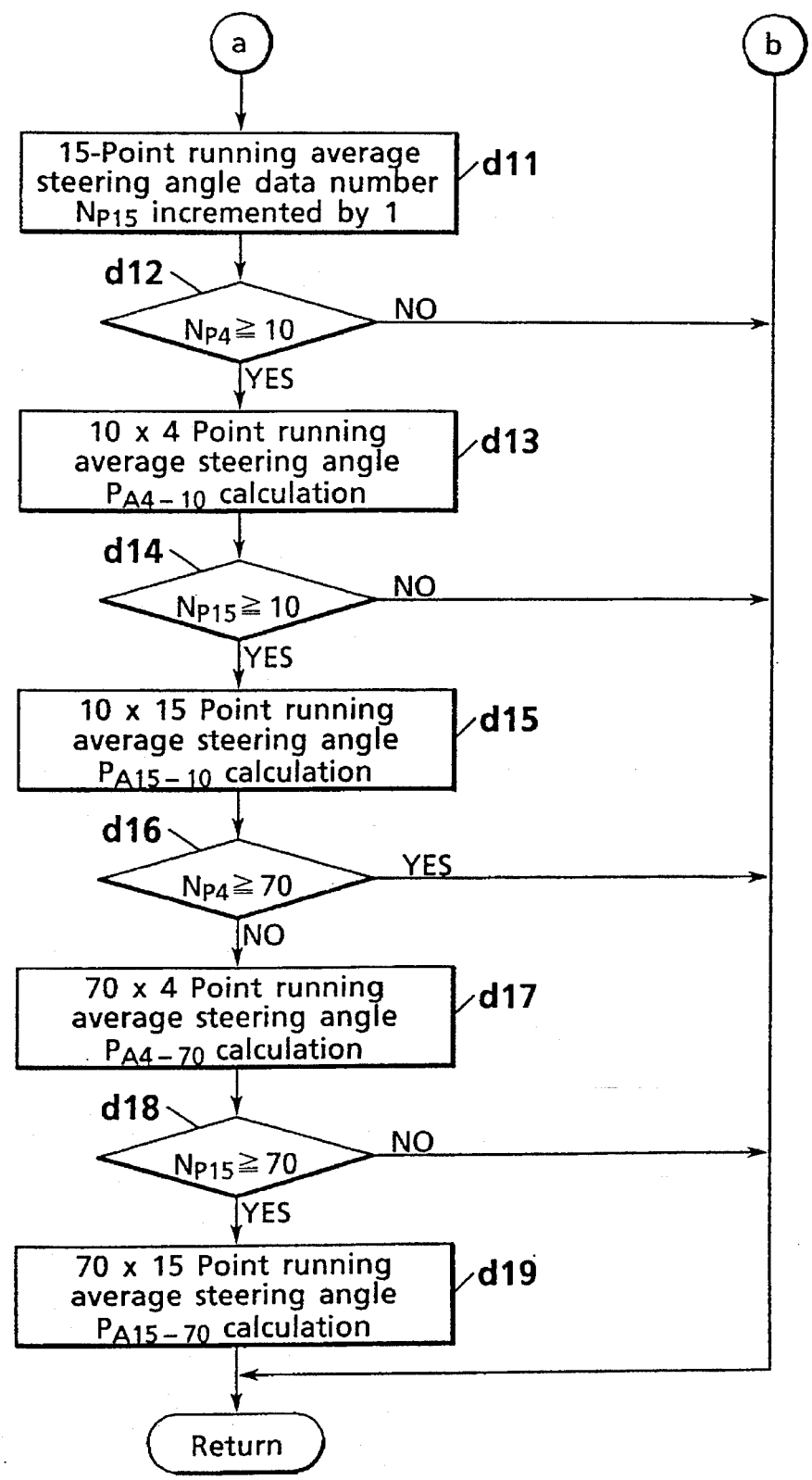
FIG. 17 is a flow chart showing processing performed by the steering angle data processing means of the present embodiment along with FIG. 16.

Processing flow in the steering angle data processing means 22 in the present embodiment is shown in FIG. 16 and FIG. 17. Specifically, processing by the steering angle data processing means 22 in the present embodiment is performed in a predetermined period, that is, upon receipt of an interrupt signal of every 15 seconds. First, in step d1, a steering angle θ from the steering angle sensor 21 and a vehicle speed V from the vehicle speed sensor 24 are read at every sample period of 0.1 second. A determination is made in step d2 as to whether or not the absolute value of the read steering angle θ is less than 10°, when it is determined that the absolute value of the steering angle θ is less than 10°, the processing proceeds to step d3. When the absolute value of the steering angle θ is determined to be 10° or more, the processing proceeds to step d4, where the past effective steering angle data number $N_S$ is reset, and the processing returns to step d1. When the vehicle is traveling with a steering angle θ of 10° or more, this is a time when the driver coarsely controls the steering wheel 33, which is not proper as data for determining the visual steering component required for determining the awareness of the driver.

A determination is made in step d3 as to whether or not the read vehicle speed V is 30 km/h or more, and when it is determined that the vehicle speed V is 30 km/h or more, the processing proceeds to step d5. When it is determined that the vehicle speed V is less than 30 km/h, the processing proceeds to step d4, where, as described above, the steering angle data number $N_S$ is reset to 0, and the processing returns again to step d1. The case when the vehicle speed V is less than 30 km/h, for example, when the vehicle travels at a low speed on a crowded road is also considered. In such a case, since the driver may perform meaningless manipulations of the steering wheel 33, data which is inappropriate for determining the awareness of the driver may be input. Therefore, as described above, when the absolute value of the steering angle θ is 10° or more or the vehicle speed V is less than 30 km/h, the read steering angle θ is not adopted in step d4.

In step d5, the effective steering angle data number $N_S$ adopted in steps d2 and d3 is incremented by 1. A determination is made in step d6 as to whether or not the effective steering angle data number $N_S$ is 4 or more, and when it is determined to be 4 or more, the processing proceeds to step d7. The 4-point running average steering angle $P_{A4}$ is calculated in step d7, and the processing proceeds to step d8, where the 4-point running average steering angle data number $N_{P4}$ of the 4-point running average steering angle $P_{A4}$ calculated in step d7 is incremented by 1. When it is determined in step d6 that the effective steering angle data number $N_S$ is not 4 or more, since the 4-point running average steering angle $P_{A4}$ cannot be calculated in step d7, the processing returns to step d1.

In step d9, a determination is made as to whether or not the effective steering angle data number $N_S$ is 15 or more, and when it is determined to be 15 or more, the processing proceeds to step d10. In step d10, the 15-point running average steering angle $P_{A15}$ is calculated, and the processing proceeds to step d11, where the 15-point running average steering angle $P_{A15}$ is incremented by 1. When it is determined in step d9 that the 15-point running average steering angle data number $N_S$ is not 15 or more, since the 15-point running average steering angle $P_{A15}$ cannot be calculated in step d10, the processing returns to step d1.

In step d12, a determination is made as to whether or not the 4-point running average steering angle data number $N_{PA}$ is 10 or more, and when it is determined to be 10 or more, the processing proceeds to step d13, where the above-described 10×4 point running average steering angle $P_{A4-10}$ is calculated, and the processing proceeds to step d14. A determination is made in step d14 as to whether or not the 15-point running average steering angle data number $N_{P15}$ is 10 or more, and when it is 10 or more, the processing proceeds to step d15, where the above-described 10×15 point running average steering angle $P_{A15-10}$ is calculated, and the processing proceeds to d16. When it is determined in steps d12 and d14 that the 4-point running average steering angle data number $N_{P4}$ or the 15-point running average steering angle data number $N_{P15}$ is not 10 or more, since the 10×4 point running average steering angle $P_{A4-10}$ and the 10×15 point running average steering angle $P_{A15-10}$ cannot be calculated in steps d13 and d15, the processing returns to step d1.

In step d16, a determination is made as to whether or not the 4-point running average steering angle data number $N_{P4}$ is 70 or more, and when it is determined to be 70 or more, the processing proceeds to step d17, where the above-described 70×4 point running average steering angle $P_{A4-70}$ is calculated, and the processing proceeds to step d18. A determination is made in step d18 as to whether or not the 15-point running average steering angle data number $N_{P15}$ is 70 or more, and when it is 70 or more, the processing proceeds to step d19, where the above-described 70×15 point running average steering angle $P_{A15-70}$ is calculated. When it is determined in steps d16 and d18 that the 4-point running average steering angle data number $N_{P4}$ or the 15-point running average steering angle data number $N_{P15}$ is not 70 or more, since the 70×4 point running average steering angle $P_{A4-70}$ and the 70×15 point running average steering angle $P_{A15-70}$ cannot be calculated in steps d17 and d19, the processing returns to step d1.

The steering awareness determination means 23 determines the present awareness of the driver according to the reference value (hereinafter referred to as "reference parameter") of a steering component frequency analyzed in the to reflect the awareness of the driver calculated by the steering angle data processing means 22, and sets the warning level corresponding to the awareness level. That is, from the 10×4 point average steering angle $P_{P4-10}$ and the 70×4 point running average steering angle $P_{A4-70}$, and the 10×15 point running average steering angle $P_{A15-10}$ and the 70×15 point running average steering angle $P_{A15-70}$, parameters $P_{S10}$ and $P_{S70}$ of the visual steering component area S are calculated by the following equations:

$$P_{S10} = |P_{A4-10} - P_{A15-10}|,$$

$$P_{S70} = |P_{A4-70} - P_{A15-70}|.$$

Then, the parameters $P_{S10}$ and $P_{S70}$ of the visual steering component area S are compared with preset reference parameters to determine the level of awareness of the driver.

Figure 18:
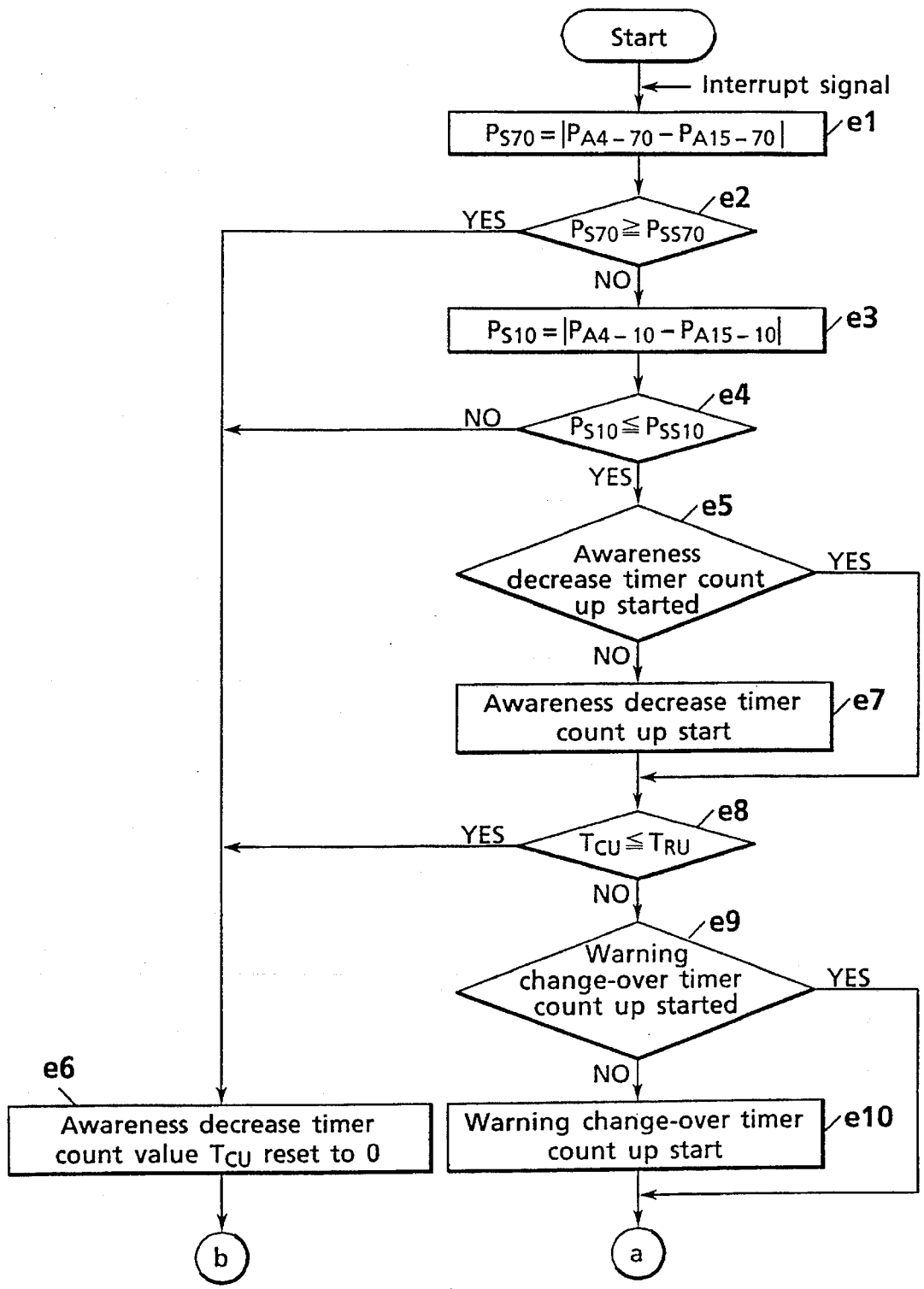
FIG. 18 is a flow chart showing processing performed by the steering awareness determination means of the present embodiment along with FIG. 19.
Figure 19:
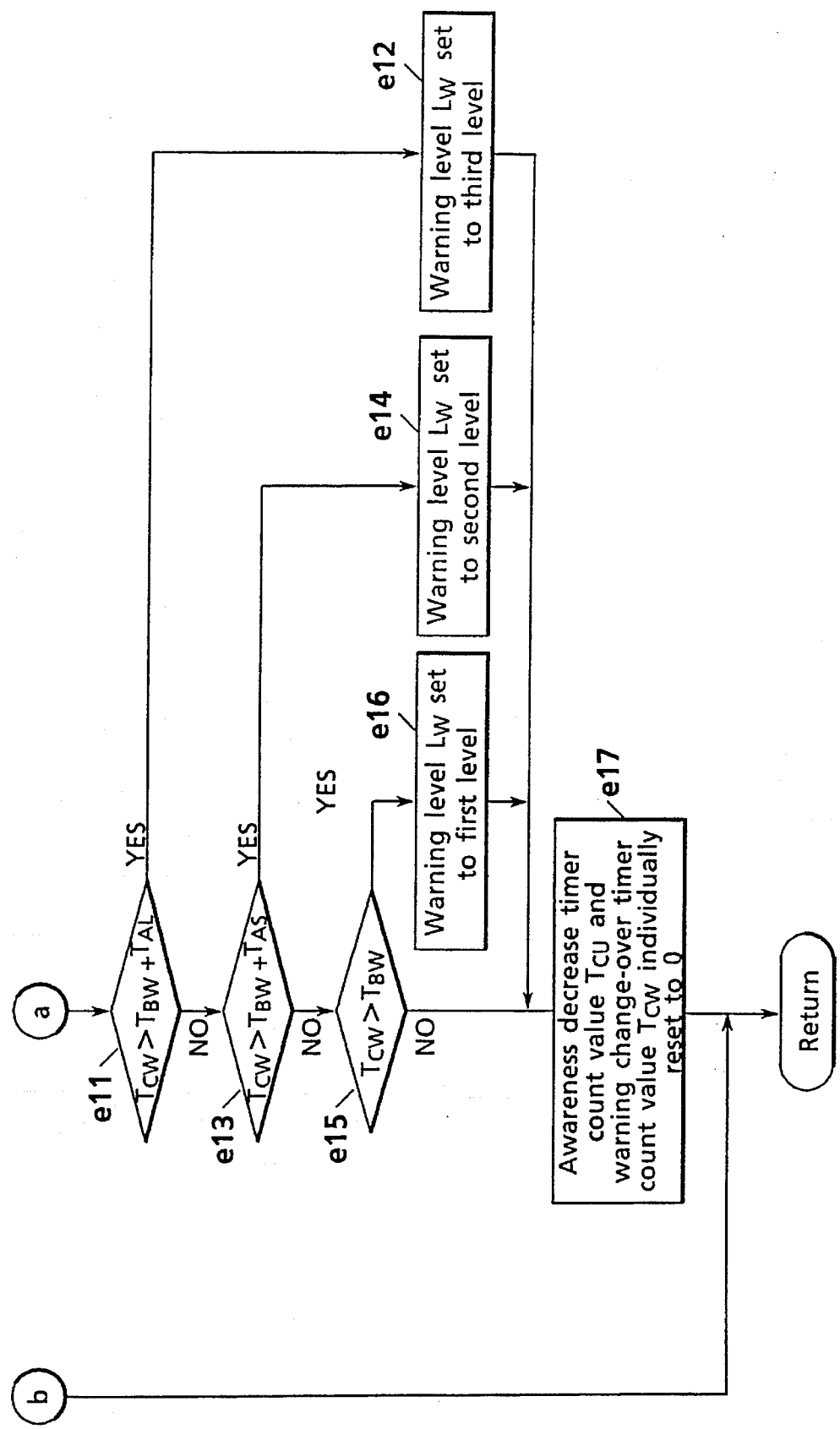
FIG. 19 is a flow chart showing processing performed by the steering awareness determination means of the present embodiment along with FIG. 18.

The processing flow in the steering awareness determination means 23 in the present embodiment is shown in FIG. 18 and FIG. 19. Specifically, processing in the steering awareness determination means 23 in the present embodiment is carried out at every interrupt signal, for example, of 15 msec. First, in step e1, the parameter $P_{S70}$ of the visual steering component area S is calculated from the absolute value of difference between the 70×4 point running average steering angle $P_{A4-70}$ and the 70×15 point running average steering angle $P_{A10-70}$. A determination is made in step e2 as to whether or not the calculated parameter $P_{S70}$ of the visual steering component area S is not less than the reference parameter $P_{SS70}$, and when the parameter $P_{S70}$ of the visual steering component area S is less than the reference parameter $P_{SS70}$, the processing proceeds to step e3.

In step e3, the parameter $P_{S10}$ of the visual steering component area S is calculated from the absolute value of difference between the 10×4 point running average steering angle $P_{A4-10}$ and the 10×15 point running average steering angle $P_{A10-10}$. A determination is made in step e4 as to whether or not the parameter $P_{S10}$ of the visual steering component area S is not more than the reference parameter $P_{SS10}$, and when the parameter $P_{S10}$ of the visual steering component area S is not more than the reference parameter $P_{SS10}$, the processing proceeds to step e5.

The reference parameter is set according to the level of awareness of the driver and, in the present embodiment, 0.21 is set as the reference parameter $P_{SS70}$ corresponding to the visual steering component parameter $P_{S70}$ and 0.17 is set as the reference parameter $P_{SS10}$ corresponding to the visual steering component parameter $P_{S10}$. The calculated parameters $P_{S10}$ and $P_{S70}$ of the visual steering component area S are compared with the reference parameters $P_{SS70}$ and $P_{SS10}$ to set the warning level $L_W$. The reference parameters $P_{SS70}$ and $P_{SS10}$, as described above, are set according to the graph shown in FIG. 13 showing the visual steering components of traveling where the awareness of the driver is low and traveling where the awareness level of the driver is high relative to the frequency distribution. These values are not limited to those in the above embodiment, but may be appropriately set according to various conditions.

When it is determined that the parameter $P_{S70}$ of the visual steering component area S calculated in step e2 is greater than the reference parameter $P_{SS70}$, the processing proceeds to step e6. When it is determined that the parameter $P_{S10}$ of the visual steering component area S calculated in step e4 is greater than the reference parameter $P_{SS10}$, the processing proceeds to step e6. In step e6, since the level of awareness of the driver is determined to be high, the count value $T_{CU}$ of the awareness decrease timer is reset to 0, and step e1 is repeated according to the next interrupt signal.

In step e5, a determination is made as to whether or not the awareness decrease timer begins counting up and, when it is determined not to be counting up, counting up of the awareness decrease timer is begun in step e7, a determination is made in step e8 as to whether or not the count value $T_{CU}$ of the awareness decrease timer is not more than a preset time $T_{RU}$, for example, 3 seconds, that is, $P_{S70} \geq P_{SS70}$ and $P_{S10} \geq P_{SS10}$. When it is determined to be not more than the preset time $T_{RU}$, the processing proceeds to step e6, where the count value $T_{CU}$ of the awareness decrease timer is reset to 0, otherwise, the processing proceeds to step e9.

In step e9, a determination is made as to whether or not a warning change-over timer begins counting up and, when it is determined not to be counting up, counting up of the warning change-over timer begins in step e10, and a determination is made in step e11 as to whether or not the count value $T_{CW}$ of the warning change-over timer is longer than a preset reference warning change-over time $T_{BW}$ added with a preset first additional time $T_{AL}$, for example, 4 seconds. When it is determined that the count value $T_{CW}$ of the warning change-over timer is longer than the sum of the reference warning change-over time $T_{BW}$ and the first additional time $T_{AL}$, that is, the awareness level of the driver decreases to its lowest level, the processing proceeds to step e12, where the warning level $L_W$ is set to the third level, and the processing proceeds to step e17 which will be described later.

When it is determined in step e11 that the count value $T_{CW}$ of the warning change-over timer is not longer than the sum of the reference warning change-over time $T_{BW}$ and the first additional time $T_{AL}$, the processing proceeds to step e13, where a determination is made as to whether or not the count value $T_{CW}$ of the warning change-over timer is longer than the sum of the reference warning change-over time $T_{BW}$ and a preset second additional time $T_{AS}$, for example, 3 seconds. When it is determined that the count value $T_{CW}$ of the warning change-over timer is longer than the sum of the reference warning change-over time $T_{BW}$ and the second additional time $T_{AS}$, the processing proceeds to step e14, where the warning level $L_W$ is set to the second level.

When it is determined in step e13 that the count value $T_{CW}$ of the warning change-over timer is not longer than the sum of the reference warning change-over time $T_{BW}$ and the second additional time $T_{AS}$, the processing proceeds to step e15, where a determination is made as to whether or not the count value $T_{CW}$ of the warning change-over timer is longer than the reference warning change-over time $T_{BW}$. When it is determined that the count value $T_{CW}$ of the warning change-over timer is longer than the reference warning change-over time $T_{BW}$, the processing proceeds to step e16, where the warning level $L_W$ is set to the first level, and the processing proceeds to step e17 which will be described later.

When it is determined in step e14 that the count value $T_{CW}$ of the warning change-over timer is not more than the reference warning change-over time $T_{BW}$, the processing proceeds to step e17, where the count value $T_{CU}$ of the awareness decrease timer and the count value $T_{CW}$ of the warning change-over time are individually set to 0, and then the step of e1 is repeated according to the next interrupt signal.

In the tactile warning means 26, a pair of right and left side supports 44 provided in the seat back 49 of the driver's seat 25 are made rotatable in the direction of the arrow to repeatedly press the driver's side sitting on the seat 25 from both sides, or separate the side supports 44 from the driver's side, thereby improving the awareness of the driver by tactile excitation. The device is adapted to operate when the driver's grip of the steering wheel 33 is not correct, or according to the warning level $L_W$ of the first level.

Further, in the visual warning means 28, a display 45 for displaying a sleep drive warning is embedded in the front window 27 in front of the driver's seat 25 which is transparent and does not block the driver's sight when unenergized and, when energized, a sleep warning mark 46 as shown in FIG. 2, for example, is turned on and off in the transparent condition, thereby improving the awareness of the driver by visual excitation. The device is adapted to operate according to the warning level $L_W$ of the second level.

Further, the auditory warning means 29 sounds a warning buzzer 48 incorporated in an instrument panel 47 to improve the awareness of the driver by auditory excitation. The device is adapted to operate when the driver's grip of the steering wheel 33 is not correct, or according to the warning level $L_W$ of the third level.

The steering wheel grip defect warning means 34 in the present embodiment, as described above, operates in conjunction with the two warning means 26 and 29. By changing the movement of the side supports 44 and the sound of the warning buzzer 48, the driver can easily distinguish between when the steering wheel 39 is gripped incorrectly and when the awareness level of the driver is decreasing.

The warning control means 30 controls operation of the three warning means 26, 28, and 29 according to the warning levels $L_W$ individually determined by the heartbeat awareness determination means 19 and the steering awareness determination means 23. When an ON operation signal of the warning release switch 31 is input by the driver, the operation of the three warning means 26, 28, and 29 according to the warning level $L_W$ is stopped. However, when the warning means 26 and 29 are operated as the steering wheel grip defect warning means 94, the operation of these devices is not stopped even if the driver turns on the warning release switch 31.

Figure 20:
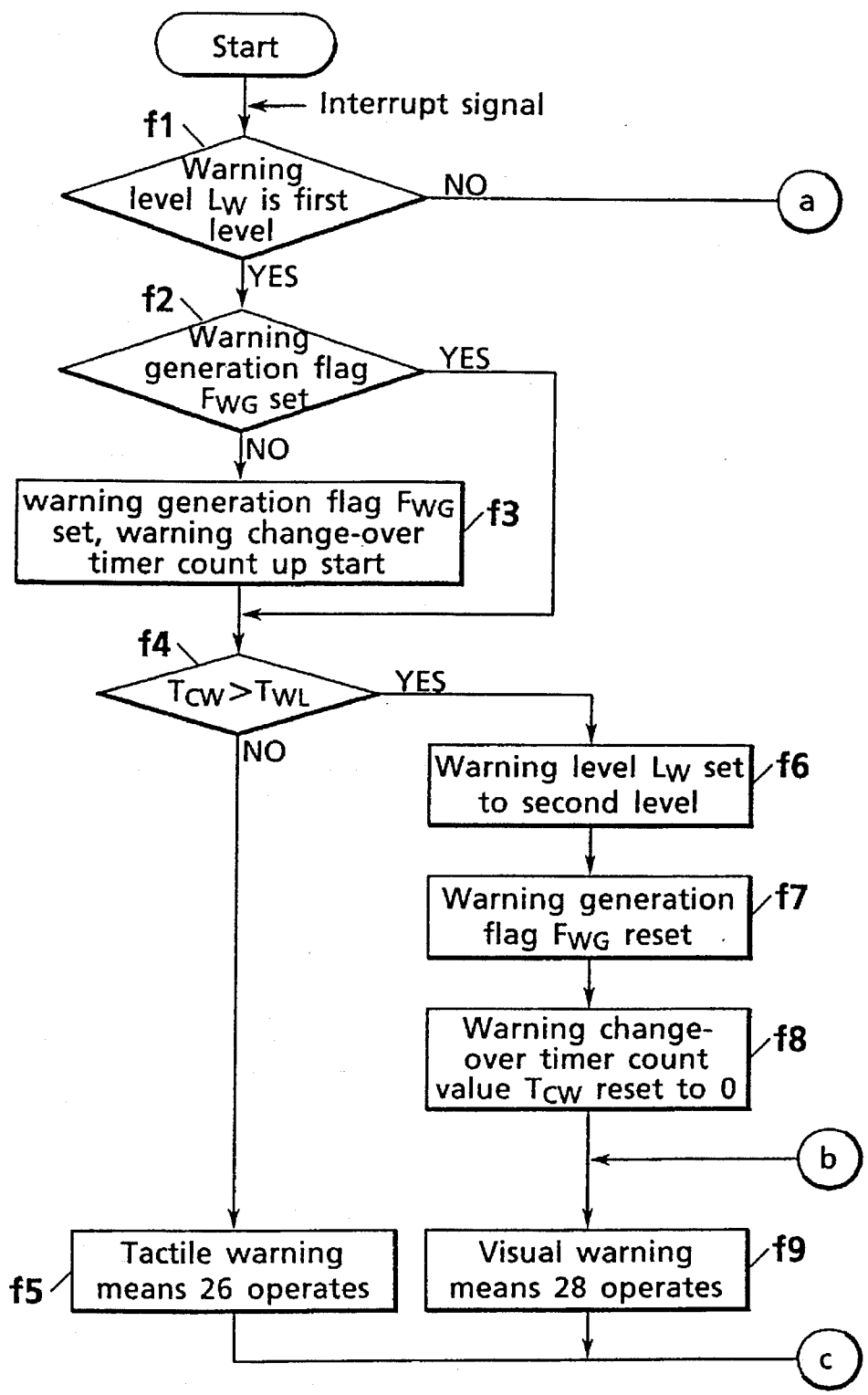
FIG. 20 is a flow chart showing warning processing performed by the warning control means of the present embodiment along with FIG. 21.
Figure 21:
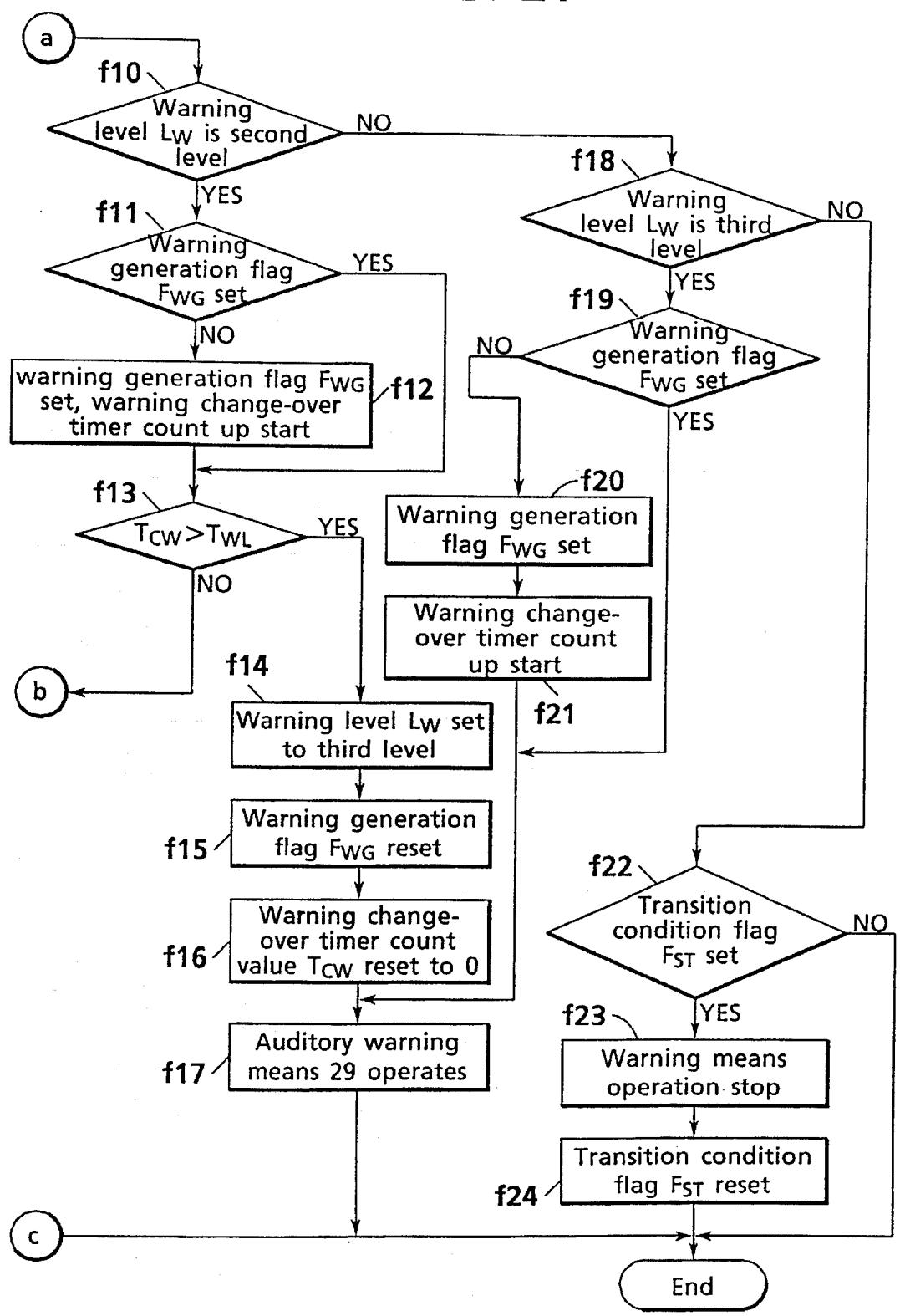
FIG. 21 is a flow chart showing warning processing performed by the warning control means of the present embodiment along with FIG. 20.

A warning processing flow of the warning control means 30 is shown in FIG. 20 and FIG. 21. Specifically, warning processing in the present embodiment is carried out for every interrupt signal of 15 msec, for example. First, a determination is made in step f1 as to whether or not the warning level $L_W$ is the first level, and when the warning level $L_W$ is the first level, the processing proceeds to step f2, where a determination is made as to whether or not a warning generation flag $F_{WG}$ is set. When it is determined in step f2 that the warning generation flag $F_{WG}$ is not set, the warning generation flag $F_{WG}$ is set in step f3, and counting up of the warning change-over timer begins, and a determination is made in step f4 as to whether or not the count value $T_{CW}$ of the warning change-over timer exceeds the first preset time $T_{WL}$, for example, 10 seconds.

When it is determined in step f4 that the count value $T_{CW}$ of the warning change-over timer is not more than the first preset time $T_{WL}$, the processing proceeds to step f5, where the tactile warning means 26 is operated to press or separate the side supports 44 relative to the side of the driver, thereby improving the awareness of the driver by tactile excitation, and the processing returns to step f1 according to the next interrupt signal.

When it is determined in step f2 that the warning generation flag $F_{WG}$ is set, the processing proceeds to step f4, where a determination is made again as to whether or not the count value $T_{CW}$ of the warning change-over timer exceeds the first preset time $T_{WL}$.

When it is determined in step f4 that the count value $T_{CW}$ of the warning change-over timer exceeds the first preset time $T_{WL}$, that is, the awareness of the driver is not improved by only the operation of the tactile warning means 26, the processing proceeds to step f6, where the warning level $L_W$ is set level, the warning generation flag $F_{WG}$ is reset to 0 in step f7, the count value $T_{CW}$ of the warning change-over timer is reset to 0 in step f8, the visual warning means 28 is operated in step f9 to display the warning mark 46 on the front window 27 to improve the awareness of the driver by visual excitation, and the processing returns to step f1 according to the next interrupt signal.

When it is determined in step f1 that the warning level $L_W$ is not the first level, the processing proceeds to step f10, where a determination is made as to whether or not the warning level $L_W$ is the second level. When it is determined in step f10 that the warning level $L_W$ is the second level, the processing proceeds to step f11, where a determination is made as to whether or not the warning generation flag $F_{WG}$ is set. When it is determined in step f11 that the warning generation flag $F_{WG}$ is not set, the warning generation flag $F_{WG}$ is set in step f12 and the warning change-over timer begins counting up, and a determination is made in step f13 as to whether or not the count value $T_{CW}$ of the warning change-over timer exceeds the first preset time $T_{WL}$.

When it is determined in step f13 that the count value $T_{CW}$ of the warning change-over timer is not more than the first preset time $T_{WL}$, the processing proceeds to step f9, where the visual warning means 28 is operated to display the warning mark 46 on the front window 27 to improve the awareness of the driver. When it is determined in step f11 that the warning generation flag $F_{WG}$ is set, the processing proceeds to step f13, where a determination is made again as to whether or not the count value $T_{CW}$ of the warning change-over timer exceeds the first preset time $T_{WL}$.

When it is determined in step f13 that the count value $T_{CW}$ of the warning change-over timer exceeds the first preset time $T_{WL}$, that is, the awareness of the driver is not improved by only the operation of the visual warning means 28, the processing proceeds to step f14, where the warning level $L_W$ is set to the third level, the warning generation flag $F_{WG}$ is reset in step f15 and the count value $T_{CW}$ of the warning change-over timer is reset to 0 in step f16, the auditory warning means 29 is operated in step f17 to sound the warning buzzer 48 to improve the awareness of the driver by auditory excitation, and then the processing returns to step f1 according to the next interrupt signal.

When it is determined in step f10 that the warning level $L_W$ is not the second level, the processing proceeds to step f18, where a determination is made as to whether or not the warning level $L_W$ is the third level. When it is determined in step f18 that the warning level $L_W$ is the third level, the processing proceeds to step f19, where a determination is made as to whether or not the warning generation flag $F_{WG}$ is set. When it is determined in step f19 that the warning generation flag $F_{WG}$ is set, the processing proceeds to step f17, where the auditory warning means 29 is operated to sound the warning buzzer 48 to improve the awareness of the driver. Further, when it is determined in step f19 that the warning generation flag $F_{WG}$ is not set, the processing proceeds to step f20, where the warning generation flag $F_{WG}$ is set, counting up of the warning change-over timer begins in step f21, and then the processing proceeds to step f17.

On the other hand, when it is determined in step f18 that the warning level $L_W$ is not the third level, the processing proceeds to step f22, where a determination is made as to whether or not the transition condition flag $F_{ST}$ is set. When it is determined that the transition condition flag $F_{ST}$ is set, operation of all three warning means 26, 28, and 29 is stopped in step f23, and the transition condition flag $F_{ST}$ is reset in step f24. When it is determined in step f22 that the transition condition flag $F_{ST}$ is not set, the processing returns to step f1 according to the next interrupt signal.

A steering wheel grip defect warning processing unit 35 incorporated in the warning control means 30 estimates a grip of the steering wheel 33 by the driver according to information of an input normal determination flag $F_{NI}$ which is set by the heartbeat processing means 13, 14, and 17 and controls the operation of the steering wheel grip defect warning means 34. When a condition where the input normal determination flag $F_{NI}$ is not set continues for a predetermined time, first, the steering wheel grip defect warning means 34 controls the tactile warning means 26 to alert the driver and, if unsuccessful, the steering wheel grip defect warning means 34 further operates the auditory warning means 29.

Figure 22:
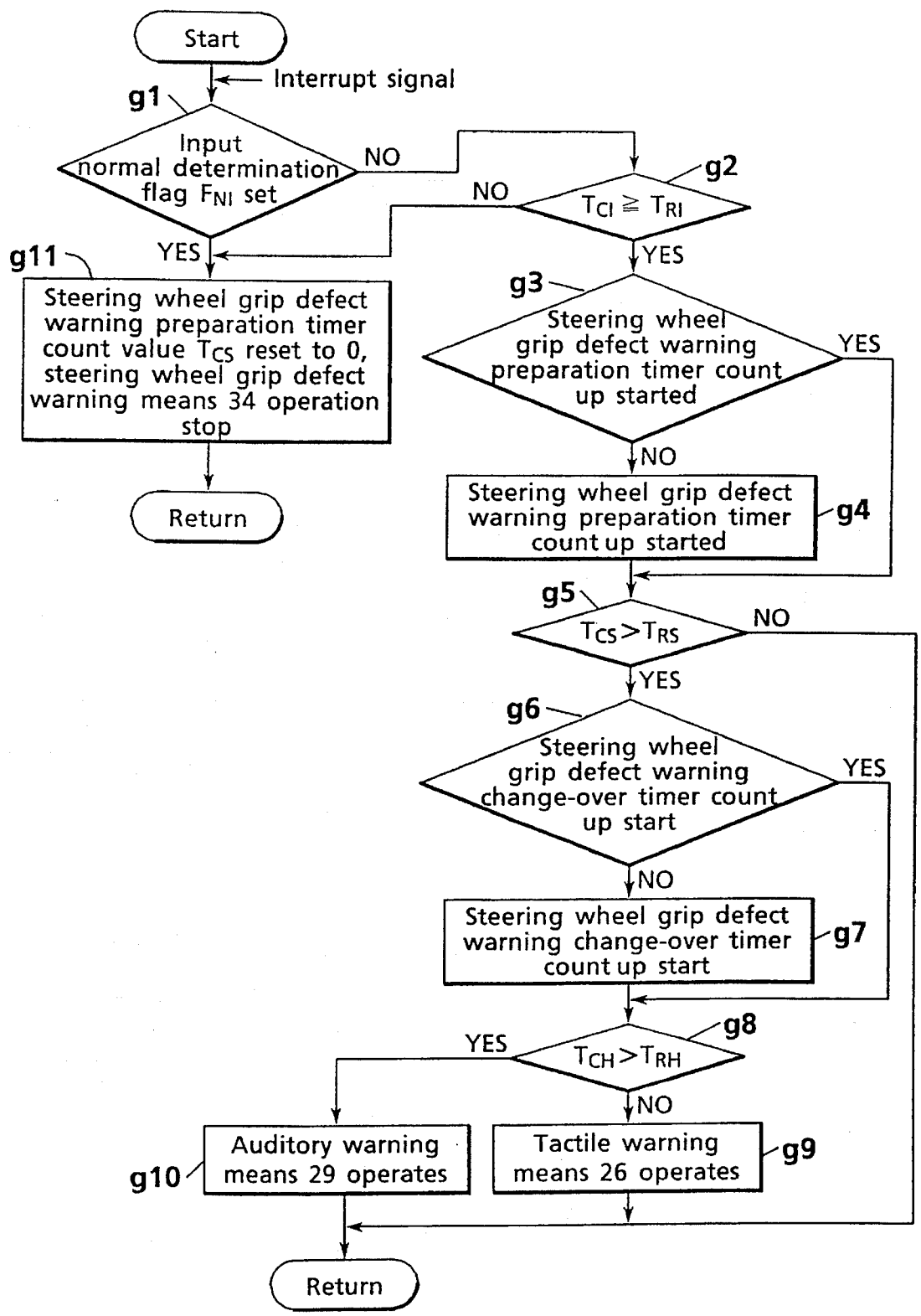
FIG. 22 is a flow chart showing processing performed by the steering wheel grip defect warning processing unit of the present embodiment.

Processing flow in the steering wheel grip defect processing unit 35 of the present embodiment according to information from the heartbeat processing means 17 is shown in FIG. 22. Specifically, processing by the steering wheel grip defect processing unit 35 in the present embodiment is carried out at every interrupt signal, for example, of 15 msec. First, a determination is made in step g1 as to whether or not the input normal determination flag $F_{NI}$ is set by the heartbeat processing means 13, 14, and 17, and when the input normal determination flag $F_{NI}$ is not set, that is, the driver's grip of the steering wheel 33 may be incorrect, the processing proceeds to step g2, where a determination is made as to whether or not the count value $T_{CI}$ of an input defect integrating timer is not less than a preset time $T_{RI}$.

When it is determined in step g2 that the count value $T_{CI}$ of the input defect integrating timer is not less than the preset time $T_{RI}$, a determination is made in step g3 as to whether or not counting up of a steering wheel grip defect warning preparation timer has begun. When it is determined that counting up of the steering wheel grip defect warning preparation timer has not begun, counting up of the steering wheel grip warning preparation timer has begun in step g4, and a determination is made in step g5 as to whether or not the count value $T_{CS}$ of the steering wheel grip defect warning preparation timer exceeds a preset time $T_{RS}$, for example, 2 seconds. Further, when it is determined in step g3 that counting up of the steering wheel grip defect warning preparation timer has begun, the processing proceeds to step g5, where a determination is made as to whether or not the count value $T_{CS}$ of the steering wheel grip defect warning preparation timer exceeds a preset time $T_{RS}$.

When it is determined in step g5 that the count value $T_{CS}$ of the steering wheel grip defect warning preparation timer exceeds a preset time $T_{RS}$, the processing proceeds to step g6, where a determination is made as to whether or not counting up of the steering wheel grip defect warning preparation timer has begun. When it is determined that counting up of the steering wheel grip defect warning preparation timer has not begun, the processing proceeds to step g7, where counting up of the steering wheel grip defect warning preparation timer is begun, and a determination is made in step g8 as to whether or not the count value $T_{CH}$ of the steering wheel grip defect warning change-over timer exceeds a preset time $T_{RH}$, for example, 3 seconds. Further, when it is determined in step g6 that the steering wheel defect warning change-over timer begins counting up, the processing proceeds to step g8, where a determination is made as to whether or not the count value $T_{CH}$ of the steering wheel grip defect warning change-over timer exceeds the preset time $T_{RH}$.

When it is determined in step g8 that the count value $T_{CH}$ of the steering wheel grip defect warning change-over timer is not more than the preset time $T_{RH}$, that is, a time duration where a grip of the steering wheel 33 is incorrect is short, the processing proceeds to step g9, where the tactile warning means 26 is operated to press or separate the side supports 44 to draw the driver's attention to grip the steering wheel 33 correctly, and the processing returns to step g1 according to the next interrupt signal.

When it is determined in step g8 that the count value $T_{CH}$ of the steering wheel grip defect warning change-over timer exceeds the preset time $T_{RH}$, that is, the driver's attention cannot be drawn by only the operation of the tactile warning means 26, the processing proceeds to step g10, where the auditory warning means 28 is operated, while pressing or separating the side supports 44 to the side of the driver, to sound the warning buzzer to draw the driver's attention to grip the steering wheel 33 correctly, by both tactile and auditory warning, and the processing returns to step g1 according to the next interrupt signal.

When it is determined in step g5 that the count value $T_{CS}$ of the steering wheel grip defect warning preparation timer is not more than the preset time $T_{RS}$, the processing returns to step g1 according to the next interrupt signal. When it is determined in step g1 that the input normal determination flag $F_{NI}$ is set, that is, the driver grips the steering wheel 33 correctly, or in step g2 that the count value $T_{CI}$ of the input defect integrating timer is less than the preset time $T_{RI}$, the processing proceeds to step g13, where the count value $T_{CS}$ of the steering wheel grip defect warning preparation timer is reset to 0, operation of the steering wheel grip defect warning means 34 is stopped, and the processing returns to step g1 according to the next interrupt signal.

The processing flow of the steering wheel grip defect warning processing unit 35 according to information from the heartbeat processing means 17 corresponding to the potential heartbeat sensor 16 has been described above with reference to FIG. 22. Similar warning processing may be performed in the steering wheel grip defect warning processing unit 35 according to information from the heartbeat processing means 13 and 14 corresponding to the infrared heartbeat sensors 11 and 12.

The reference value correction unit 32 determines according to a time from operation of the warning means 26, 28, and 29 to the driver's operation of the warning release switch 31, that the awareness of the driver is relatively high when the time is short, and corrects the reference heartbeat rate $R_{HB}$ and the reference warning change-over time $T_{BW}$ to higher values. On the other hand, when the time from operation of the warning means 26, 28, and 29 to the driver's operation of the warning is long, it determines that the awareness of the driver is lower than expected, corrects the reference heartbeat rate $R_{HB}$ and the reference warning change-over time $T_{BW}$ to lower values so that the warning means 26, 28, and 29 operate earlier, and outputs the corrected reference heartbeat rate $R_{HB}$ and the reference warning change-over time $T_{BW}$ individually to the heartbeat awareness determination means 19 and the steering awareness determination means 23.

Figure 23:
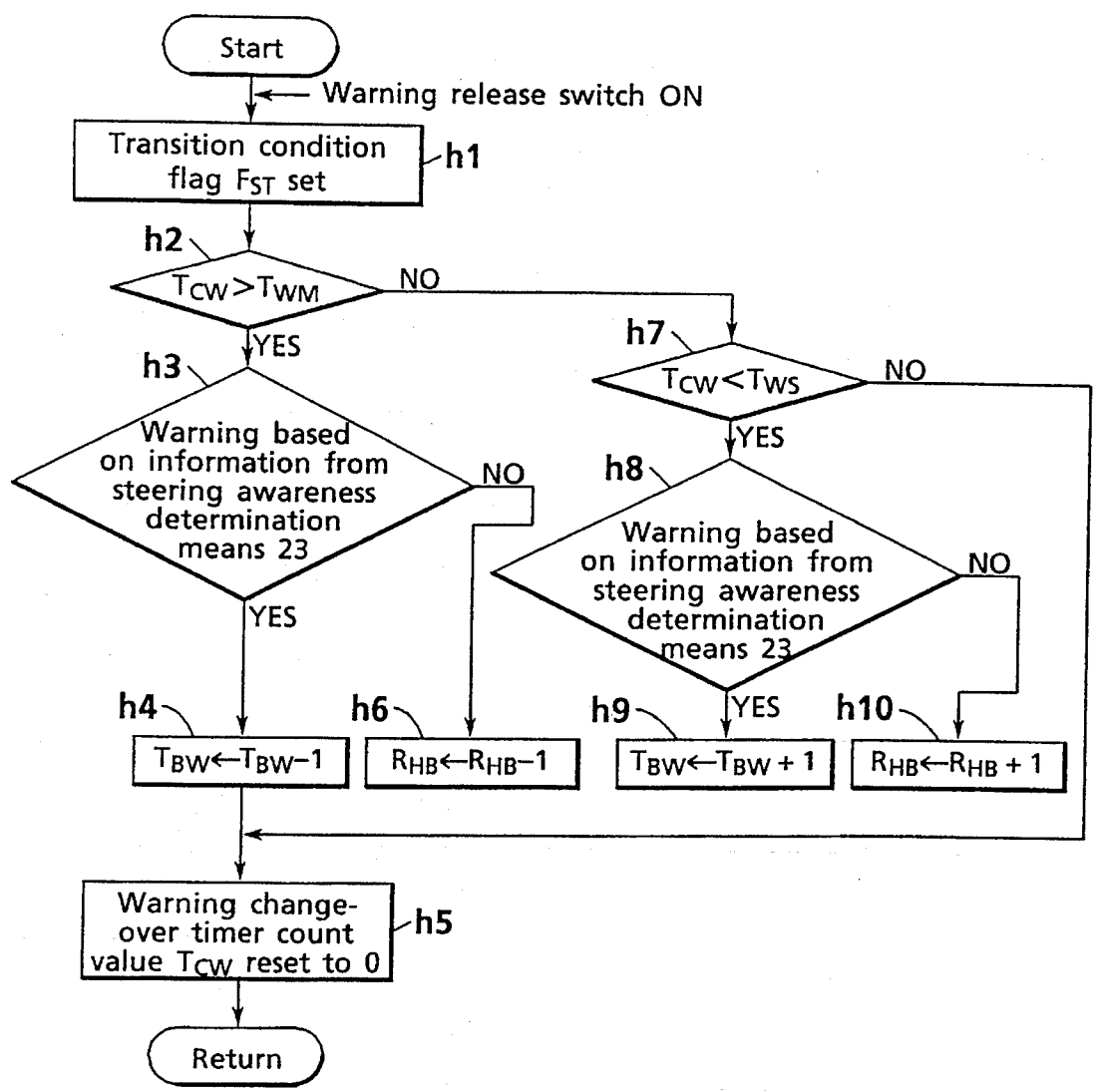
FIG. 23 is a flow chart showing processing performed by the reference value correction unit of the present embodiment.

Processing flow in the reference value correction unit 32 in the present embodiment is shown in FIG. 23. The processing in the reference value correction unit 32 in the present embodiment is begun by turning on the warning release switch 31. First, in step h1, the warning release flag $F_{ST}$ is set, and determination is made in step h2 as to whether or nor the count value $T_{CW}$ of the warning change-over timer exceeds a second preset time $T_{WM}$, for example, 6 seconds.

When it is determined in step h2 that the count value $T_{CW}$ of the warning change-over timer exceeds the second preset time $T_{WM}$, that is, reaction of the driver is not very fast, the processing proceeds to step h3, where a determination is made as to whether or not the present warning is a result of information from the steering awareness determination means 29. When it is determined that the warning is according to information from the steering awareness determination means 2S, the processing proceeds to step h4, where the reference warning change-over time $T_{BW}$ is re-set to a 1 second smaller value so that the warning means 26, 28, and 29 operate earlier than before. Further, the count value $T_{CW}$ of the warning change-over timer is reset to 0, and then the processing returns to step h1 according to the next interrupt signal. When it is determined in step h9 that the present warning is not a result of information from the steering awareness determination means 23, that is, the warning is a result of information from the heartbeat awareness determination means 19, the processing proceeds to step h6, where the reference heartbeat rate $R_{HB}$ is re-set to a 1 smaller value so that the warning means 26, 28, and 29 operate sooner, and the count value $T_{CW}$ of the warning change-over timer is reset to 0.

On the other hand, when it is determined in step h2 that the count value $T_{CW}$ of the warning change-over timer is not more than the second preset time $T_{WM}$, the processing proceeds to step h7, where a determination is made as to whether or not the count value $T_{CW}$ of the warning change-over timer is shorter than a third preset time $T_{WS}$, for example, 2 seconds. When it is determined that the count value $T_{CW}$ of the warning change-over timer is shorter than the third preset time $T_{WS}$, that is, a reaction by the driver is very fast, the processing proceeds to step h8, where a determination is made as to whether or not the present warning is a result of information from the steering awareness determination means 23. When it is determined in step h8 that the present warning is a result of information from the steering awareness determination means 23, the processing proceeds to step h9, where the reference warning change-over time $T_{BW}$ is re-set to a 1 second greater value so that the warning means 26, 28, and 29 operate later, and then the processing proceeds to step h5. When it is determined in step h8 that the present warning is not a result of information from the steering awareness determination means 23, that is, the warning is according to information from the heartbeat awareness determination means 19, the processing proceeds to step h10, where the reference heartbeat rate $R_{HB}$ is re-set to 1 greater value so that the warning means 26, 28, and 29 operate later, and the processing proceeds to step h5.

When it is determined in step h7 that the count value $T_{CW}$ of the warning change-over timer is not less than the third preset time $T_{WS}$, the present reference heartbeat rate $R_{HB}$ and the reference warning change-over time $T_{BW}$ are unchanged, and the processing proceeds to step h5, where the count value $T_{CW}$ of the warning change-over timer is reset to 0.

As described above in detail with reference to the embodiment, with the present invention, the awareness determination means determines an index of the awareness of the driver during traveling and compares the index with a preset reference value to determine a decrease in awareness of the driver, the warning control means controls the warning means according to the output of the awareness determination means and outputs a warning to the driver if the level of awareness of the driver is low. At this moment, the reference value correction means corrects the reference value for determining the awareness according to the response time to the warning from the driver, the reference value of heartbeat rate is corrected when the awareness determination means compares the index of heartbeat of the driver during traveling with the reference value to determine a decrease in awareness, or the reference value of the steering characteristic parameter of the driver is corrected when the awareness determination means compares the steering characteristic parameter of the driver determined by frequency analyzing the steering angle of the vehicle during traveling with the reference value to determine a decrease in awareness. Therefore, the reference value of heartbeat rate or the steering characteristic parameter can be set according to the individual level of the driver, operation condition, road condition, and the like, thereby improving the accuracy of awareness determination.

We claim:

1. An apparatus comprising:

awareness determination means for determining a level of awareness of a vehicle driver and comparing the level of awareness with a reference value to determine a decrease in awareness, at least one warning means for generating a warning to the vehicle driver when the decrease in awareness is detected, warning termination means for terminating the warning upon operation by the vehicle driver, and reference value correction means for measuring a response time from the generation to the termination of said warning and for correcting the reference value of said awareness determination means according to said response time for subsequent comparison and warning generation.

2. An apparatus of claim 1, wherein said at least one warning means includes a plurality of warning means, said apparatus further comprising warning control means for selecting one of said plurality of warning means according to the level of awareness determined to generate said warning for a reference value actuation time, and warning actuation time correcting means for correcting said reference value actuation time of the selected one of said plurality of warning means according to the response time to the warning from the vehicle driver.

3. The apparatus of claim 2, wherein said warning actuation time correction means determines the level of awareness of the driver to be high when the response time is shorter than a predetermined value and corrects the reference warning actuation time such that the selected one of said plurality of warning means is delayed.

4. The apparatus of claim 2, wherein said warning actuation time correction means determines the level of awareness of the driver to be low when the response time is longer than a predetermined value and corrects the reference value of said awareness determination means such that the warning from said at least one warning signal means is generated earlier than when said response time is shorter or equal to said predetermined value.

5. The apparatus of claim 2, wherein said plurality of warning means includes, tactile warning means for increasing the level of awareness by tactile excitation when the level of awareness is in a first range, visual warning means for increasing the level of awareness by visual excitation when the level of awareness is in a second range lower than the first range, and auditory warning means for increasing the level of awareness by auditory excitation when the level of awareness is in a third range, lower than the second range.

6. The apparatus of claim 1, wherein said reference value correction mean further determines the level of awareness of the vehicle driver to be high when the response time is shorter than a predetermined value and corrects the reference value of said awareness determination means such that the warning from said at least one warning means is delayed.

7. The apparatus of claim 1, wherein said reference value correction means further determines the level of awareness of the vehicle driver to be low when the response time is longer than a predetermined value and corrects the reference value of said awareness determination means such that the warning from said at least one warning signal means is generated earlier than when said response time is shorter or equal to said predetermined value.

8. The apparatus of claim 1, wherein said awareness determination means determines the level of awareness from a heartbeat rate of the vehicle driver and a steering characteristic parameter of a steering wheel of a vehicle, said reference value correction means further correcting a reference heartbeat rate when the level of awareness is determined from the heartbeat rate and correcting a reference steering characteristic value when the level of awareness is determined from the steering characteristic parameter.

9. An apparatus comprising:

heartbeat rate detection means for detecting a heart rate of a driver of a vehicle, heartbeat awareness determination means for comparing the heartbeat rate determined by said heartbeat rate detecting means with a reference value to determine a decrease in awareness of the driver, warning means warning the driver, warning control means for controlling said warning means for generation of said warning according to the comparison by said heartbeat awareness determination means, warning termination means for terminating the warning upon operation by the vehicle driver, and reference value correction means for measuring a response time from the generation to the termination of said warning and for correcting the reference value of said heartbeat awareness determination means according to said response time for subsequent comparison and warning generation.

10. An apparatus comprising:

a steering angle sensor for detecting a steering angle of a vehicle and generating steering angle data, steering angle data processing means for calculating a frequency distribution of the steering angle data and extracting a predetermined frequency area to determine a steering characteristic parameter of the driver, steering awareness determination means for comparing the steering characteristic parameter with a reference value to determine a decrease in awareness of the driver, warning means warning the driver, warning control means for controlling said warning means for generation of said warning according to the comparison by said steering awareness determination means, warning termination means for terminating the warning upon operation by the vehicle driver, and reference value correction means for measuring a response time from the generation to the termination of said warning and for correcting the reference value of said steering awareness determination means according to said response time for subsequent comparison and warning generation.

11. A method comprising:

determining a level of awareness of a driver of a vehicle and comparing the level of awareness determined with a reference value to determine a decrease in awareness;

outputting a warning to the driver upon said determined decrease in awareness;

terminating the warning upon receipt of an operated response from the driver; and measuring a response time from the output to the termination of said warning; and correcting the reference value according to said response time to the warning from the driver for subsequent comparing and warning output.

12. An apparatus comprising:

determining means for determining a level of awareness of a driver of a vehicle and comparing the level of awareness determined with a reference value;

warning means for outputting a warning to the driver upon said determined awareness level falling below said reference value;

termination means for terminating the warning by a response operation from said driver; and correcting means for measuring a response time from the output to the termination of said warning and for correcting the reference value according to said response time to the warning from the driver for subsequent comparing and warning generation.

* * * * *